United States Patent
Reves et al.

(10) Patent No.: US 10,632,230 B2
(45) Date of Patent: *Apr. 28, 2020

(54) IMPLANTS HAVING A HIGH DRUG LOAD OF AN OXYSTEROL AND METHODS OF USE

(71) Applicant: Warsaw Orthopedic, Inc., Warsaw, IN (US)

(72) Inventors: Benjamin T. Reves, Germantown, TN (US); David S. Scher, Collierville, TN (US); Susan J. Drapeau, Collierville, TN (US); Roger E. Harrington, Collierville, TN (US); Jerbrena C. Jacobs, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/796,601

(22) Filed: Jul. 10, 2015

(65) Prior Publication Data

US 2017/0007739 A1    Jan. 12, 2017

(51) Int. Cl.
*A61L 27/24*    (2006.01)
*A61F 2/30*    (2006.01)
(Continued)

(52) U.S. Cl.
CPC .......... *A61L 27/54* (2013.01); *A61K 31/575* (2013.01); *A61K 38/1709* (2013.01); *A61K 38/1875* (2013.01); *A61L 27/10* (2013.01); *A61L 27/24* (2013.01); *A61L 27/26* (2013.01); *A61L 27/425* (2013.01); *A61L 27/446* (2013.01); *A61L 27/46* (2013.01); *A61L 27/58* (2013.01); *A61F 2210/0076* (2013.01); *A61F 2230/0069* (2013.01); *A61L 2300/222* (2013.01);
(Continued)

(58) Field of Classification Search
None
See application file for complete search history.

(56) References Cited

U.S. PATENT DOCUMENTS 4,877,864 A    10/1989    Wang et al.
5,683,459 A    11/1997    Brekke
(Continued)

FOREIGN PATENT DOCUMENTS

CN    107683130 A    2/2018
WO    2005005453 A2    1/2005
(Continued)

OTHER PUBLICATIONS

International Search Report of the International Searching Authority (ISA/KR)/Korean Intellectual Property Office dated Feb. 3, 2017 of International PCT Application No. PCT/US2016/058474 filed on Oct. 24, 2016.
(Continued)

*Primary Examiner* — Dominic Lazaro

(57) ABSTRACT

Provided is an implant configured to fit at or near a bone defect to promote bone growth, the implant comprising: a biodegradable polymer in an amount of about 0.1 wt % to about 20 wt % of the implant and an oxysterol in an amount of about 20 wt % to about 90 wt % of the implant. The implant has a high oxysterol load. Methods of making and use are further provided.

8 Claims, 7 Drawing Sheets

Post-op 4 weeks 8 weeks

(51) Int. Cl.

| | | |
|---|---|---|
| *A61L 27/10* | (2006.01) | |
| *A61L 27/54* | (2006.01) | |
| *A61L 27/36* | (2006.01) | |
| *A61F 2/28* | (2006.01) | |
| *A61L 27/58* | (2006.01) | |
| *A61L 27/44* | (2006.01) | |
| *A61L 27/46* | (2006.01) | |
| *A61K 31/575* | (2006.01) | |
| *A61K 38/17* | (2006.01) | |
| *A61K 38/18* | (2006.01) | |
| *A61L 27/26* | (2006.01) | |
| *A61L 27/42* | (2006.01) | |

(52) U.S. Cl.
CPC ... *A61L 2300/412* (2013.01); *A61L 2300/414* (2013.01); *A61L 2300/45* (2013.01); *A61L 2300/604* (2013.01); *A61L 2430/02* (2013.01)

(56) References Cited

U.S. PATENT DOCUMENTS

| | | | |
|---|---|---|---|
| 5,899,939 | A | 5/1999 | Boyce et al. |
| 6,371,992 | B1 | 4/2002 | Tanagho et al. |
| 7,897,588 | B2 | 3/2011 | Parhami |
| 8,022,052 | B2 | 9/2011 | Parhami et al. |
| 8,268,008 | B2 | 9/2012 | Betz et al. |
| 8,475,824 | B2 | 7/2013 | McKay |
| 8,586,070 | B2 | 11/2013 | Briest |
| 8,642,065 | B2 | 2/2014 | Hans Moore et al. |
| 8,758,791 | B2 | 6/2014 | McKay |
| 8,877,221 | B2 | 11/2014 | McKay |
| 8,900,617 | B2 | 12/2014 | McKay |
| 9,271,821 | B2 | 3/2016 | Roock et al. |
| 9,878,070 | B2 | 1/2018 | Reves et al. |
| 2003/0009235 | A1 | 1/2003 | Manrique et al. |
| 2003/0093157 | A1* | 5/2003 | Casares ............ A61L 27/48 623/23.73 |
| 2003/0153541 | A1* | 8/2003 | Dudley ............ A61K 31/00 514/171 |
| 2006/0067973 | A1* | 3/2006 | Schachter ........ A61L 27/44 424/426 |
| 2006/0251735 | A1 | 11/2006 | Parhami |
| 2006/0270645 | A1 | 11/2006 | Parhami |
| 2007/0248575 | A1 | 10/2007 | Connor et al. |
| 2009/0202660 | A1 | 8/2009 | Parhami |
| 2009/0220562 | A1 | 9/2009 | Parhami |
| 2010/0034781 | A1 | 2/2010 | Parhami et al. |
| 2010/0119492 | A1 | 5/2010 | Hans et al. |
| 2011/0008297 | A1 | 1/2011 | Parhami et al. |
| 2011/0028393 | A1* | 2/2011 | Vickers ............ A61K 38/1875 514/8.8 |
| 2011/0104230 | A1 | 5/2011 | Mousa et al. |
| 2011/0276147 | A1 | 11/2011 | Cook et al. |
| 2012/0107401 | A1 | 5/2012 | McKay |
| 2012/0121660 | A1* | 5/2012 | Akella ............ A61L 24/0063 424/400 |
| 2012/0195952 | A1 | 8/2012 | King |
| 2012/0219599 | A1 | 8/2012 | Moore et al. |
| 2012/0265167 | A1 | 10/2012 | Simonson et al. |
| 2013/0244942 | A1 | 9/2013 | Benedict et al. |
| 2014/0170202 | A1 | 6/2014 | Peters et al. |
| 2014/0248372 | A1 | 9/2014 | Boden et al. |
| 2014/0275394 | A1* | 9/2014 | Allen ............ C09D 133/066 524/507 |
| 2014/0335147 | A1 | 11/2014 | Alexakis |
| 2015/0118277 | A1 | 4/2015 | Parhami et al. |
| 2015/0140059 | A1 | 5/2015 | Parhami et al. |
| 2016/0159848 | A1 | 6/2016 | Harrington et al. |
| 2016/0159850 | A1 | 6/2016 | Parhami et al. |
| 2017/0022244 | A1 | 1/2017 | Parhami et al. |

FOREIGN PATENT DOCUMENTS

| | | | | |
|---|---|---|---|---|
| WO | | 2008115469 A2 | 9/2008 | |
| WO | | 2009073186 A1 | 6/2009 | |
| WO | | 2012024581 A2 | 2/2012 | |
| WO | | 2012024584 A2 | 2/2012 | |
| WO | | 2013169399 A1 | 11/2013 | |
| WO | WO | 2013169399 A1 * | 11/2013 | ............ A61K 45/06 |
| WO | | 2014093836 A1 | 6/2014 | |
| WO | | 2014179756 A1 | 11/2014 | |
| WO | | 2015009991 A2 | 1/2015 | |
| WO | | 2015014872 A1 | 2/2015 | |
| WO | | 2015168636 A1 | 11/2015 | |
| WO | | 2016205525 A1 | 12/2016 | |

OTHER PUBLICATIONS

International Search Report and Written Opinion of the ISA/US dated Apr. 8, 2016 of PCT/US2015/064526 filed Dec. 8, 2015.

Nedelcu, et al. Oxysterol binding to the extracellular domain of Smoothened in Hedgehog Signaling. Nature Chemical Biology 9(9): 557-564 (2013) Supplementary information pp. 1-28, retrieved from internet Mar. 9, 2016 from URL: http://www.nature.com/nchembio/journal/v9/n9/extref/nchembio.1290-S1.pdf, entire document.

Haren, et al. Inhibition of cholesterol side-chain cleavage by intermediates of an alternative steroid biosynthetic pathway. FEBS Letters 232(2): 377-380; 1988. Retrieved on Mar. 9, 2016 from internet URL:http//onlinelibrary.wiley.com/doi/10.1016/0014-5793(88)80773-7/epdf>, entire document.

PubChem, Compound Summary for SID 113493311, Create Date Mar. 11, 2011 retrieved from the internet Jan. 14, 2016 URL: https??pubchem.ncbi.nim.nih.gov/substance/113493311>, entire document.

International Search Report and Written Opinion of the ISA/KR dated Feb. 3, 2017 of PCT/US2016/058474 filed Oct. 24, 2016.

International Search Report and Written Opinion of the ISR/KR dated Oct. 17, 2018 of PCT/US2018/036578 filed Jun. 8, 2018.

Extended European Search Report dated Sep. 20, 2018 in European Application No. EP 18171483.3 for Oxysterol-Statin Compounds for Bone Growth, filed May 9, 2018.

Ruan, Feng, et al. Mechanisms of bone anabolism regulated by statins. Bioscience Reports, vol. 32, No. 6, Sep. 14, 2012, pp. 511-519.

Extended European Search Report dated Jul. 2, 2018 in European application EP No. 15868634.5 for Compounds and Methods Involving Sterols, filed Dec. 8, 2015.

Velgova, H., et al. On Steroids. CXXVI. Further compounds with antisclerotization effect on *Pyrrhocoris apterus* L. larvae; Structure and activity correlations. Collection Symposium Series (XIIIth Symposium on Chemistry of Nucleic Acid Components Spindleruv Mlyn, Czech Republic, Sep. 3, 2009, 2; [Collection Symposium Series] XX, XX, vol. 34, Jan. 1, 1969, pp. 3354-3376.

Montgomery, Scott R., et al. A Novel Osteogenic Oxysterol Compound for Therapeutic Development to Promote Bone Growth: Activation of Hedgehog Signaling and Osteogenesis Through Smoothened Binding. Journal of Bone and Mineral Research, vol. 29, No. 8, Aug. 21, 2014, pp. 1872-1885.

Burger, Alain, et al. Acetylenic cholesteryl derivatives as irreversible inhibitors of ecdysone biosynthesis. Tetrahedron, vol. 44, No. 4, Jan. 1, 1988, pp. 1141-1152.

Litvinovskaya, R. P., et al. Synthesis of 5[alpha]-hydroxyecdysteroid analogs containing an isoxazole ring in the side chain. Russian Journal of Organic Chemistry, Nauka/Interperiodica, MO, vol. 40, No. 10, Oct. 1, 2004, pp. 1456-1461.

Extended European Search Report dated Oct. 9, 2018 in European application No. EP 18174762.7 for Moldable Formulations Containing an Oxysterol in an Acellular Tissue Matrix, filed May 29, 2018.

Extended European Search Report dated Sep. 12, 2018 in European application No. EP 18168537.1 for Oxysterol-Therapeutic Agent Derivative for Bone Healing, filed Apr. 20, 2018.

(56) References Cited

OTHER PUBLICATIONS

Extended European Search Report dated Jul. 29, 2019 in European application No. EP 18168537.1 for Oxysterol-Therapeutic Agent Derivative for Bone Healing, filed Apr. 20, 2018.

Chinese First Office Action dated Jun. 14, 2019 in Chinese Application No. 201580076053.4 for Compounds and Methods Involving Sterols, of Warsaw Orthopedic Inc., filed Dec. 8, 2015, English translation provided.

Petrow, Vladimir, et al. 20-Hydroxycholesterol. Journal of the Chemical Soc, Chemical Society, Letchworth, GB. Jan. 1, 1956, pp. 4675-4676.

Buser, Z., et al. Effect of Oxy133, an osteogenic oxysterol, on new bone formation in rat two-level posterolateral fusion model. Eur Spine J., (2017) 26:2763-2772, May 25, 2017.

Chinese Office Action issued by the Chinese State IP Office dated Aug. 29, 2019 in Chinese Application No. 201680061753.0 for Implants Having a Drug Load of an Oxysterol and Methods of Use filed Jun. 16, 2016. English translation provided.

* cited by examiner

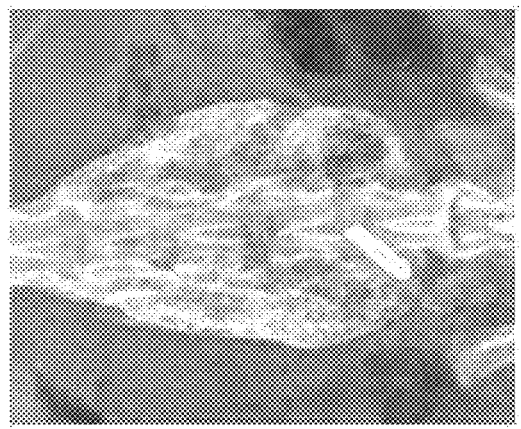
8 weeks
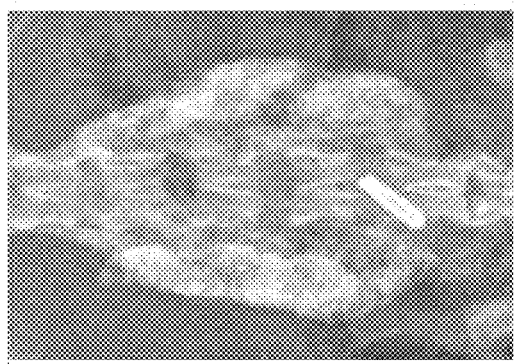
4 weeks
FIG. 7
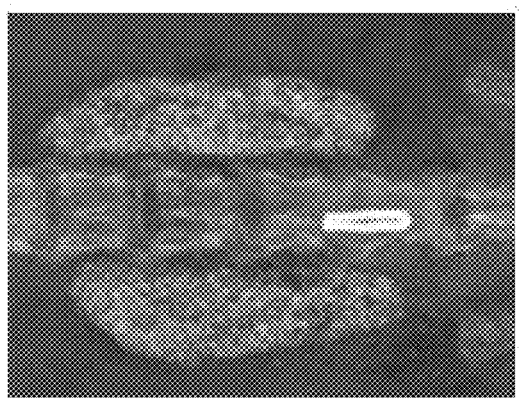
Post-op

IMPLANTS HAVING A HIGH DRUG LOAD OF AN OXYSTEROL AND METHODS OF USE

BACKGROUND

Biologics are commonly employed to promote bone growth in medical applications including fracture healing and surgical management of spinal disorders. Spine fusion is often performed by orthopedic surgeons and neurosurgeons alike to address degenerative disc disease and arthritis affecting the lumbar and cervical spine, to correct deformities caused by scoliosis, and to repair instability due to spondylolisthesis. Additionally, the techniques of spinal fusion may be applied to treat arm or leg pain caused by compressed spinal nerves. Historically, autogenous bone grafting, commonly taken from the iliac crest of the patient, has been used to augment fusion between vertebral levels.

One protein that is osteogenic and commonly used to promote spine fusion is recombinant human bone morphogenetic protein-2 (rhBMP-2). Small molecules have also been use to induce bone growth. Oxysterols form a large family of oxygenated derivatives of cholesterol that are present in the circulation, and in human and animal tissues. Oxysterols have been found to be present in atherosclerotic lesions and play a role in various physiologic processes, such as cellular differentiation, inflammation, apoptosis, and steroid production. Some naturally occurring oxysterols have robust osteogenic properties and can be used to grow bone. The most potent osteogenic naturally occurring oxysterol, 20(S)-hydroxycholesterol, is both osteogenic and anti-adipogenic when applied to multipotent mesenchymal cells capable of differentiating into osteoblasts and adipocytes.

One such oxysterol is Oxy133 or (3S,5S,6S,8R,9S,10R, 13S,14S,17S)17-((S)-2-hydroxyoctan-2-yl)-10,13-dimethylhexadecahydro-1H-cyclopenta[a]phenanthrene-3,6-diol, which exhibits the following structures:

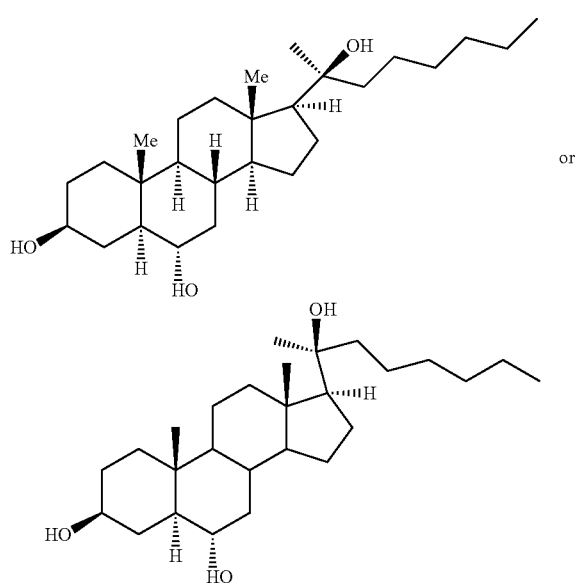

A variety of materials have been suggested for the treatment of bone defects. In addition to traditional bone grafting, a number of synthetic bone graft substitutes have been used or explored, including several matrix materials.

To conduct bone growth effectively, implant materials derive benefit from the presence of substantial scaffolding material such as biocompatible ceramics or other mineral scaffolds. Such mineral materials are generally hard, and/or brittle substances. The incorporation of substantial levels of mineral particles into matrix materials, particularly if the mineral particles are granules or other relatively large particles, may be difficult because the large particles of hard minerals tend to disrupt the matrix mass such that it is readily broken or eroded away, and lacks cohesiveness desired for handling prior to implant and for persistence after implant. This may present problems in achieving effective bone growth into and through the desired implant volume, due to migration or separation of the scaffolding particulates. Additionally, carrier scaffolds with high amounts of ceramics are rigid and typically cannot fit into irregularly shaped bone defects.

Therefore, there exist needs for improved malleable implants which not only have high levels of incorporated, mineral particles, but also maintain the desired combination of malleability and cohesiveness. Additionally, there is a need to provide malleable implants which incorporate an osteogenic agent, such as an oxysterol. Furthermore, there is also a need for a malleable implant having adhesive properties to bind to other medical implants such as screws, rods, plates, and interbody devices comprising bone, allograft, autograft, synthetic materials and/or PEEK.

SUMMARY

Implants having a high load of oxysterol and methods of making and using those implants are provided. The implants can be formed to fit easily within a bone defect. In some embodiments, the implants have mineral particles incorporated within them and also maintain the desired combination of malleability and cohesiveness. Additionally, provided are malleable implants which incorporate an osteogenic agent, such as an oxysterol. In one aspect, the present application is directed to an implantable osteogenic medical material comprising a malleable and cohesive implant that includes a combination of a biodegradable polymer, mineral particles and an active agent comprising an oxysterol. In another aspect, the present application is directed to a malleable implant having adhesive properties to bind to other medical implants such as screws, rods, plates, and interbody devices comprising bone, allograft, autograft, synthetic materials and/or PEEK.

In some embodiments, the malleable implant can be a robust implant that can have a high mineral content or allograft content, still bind and be cohesive.

In some embodiments, provided is a malleable implant having an active agent comprising the structure:

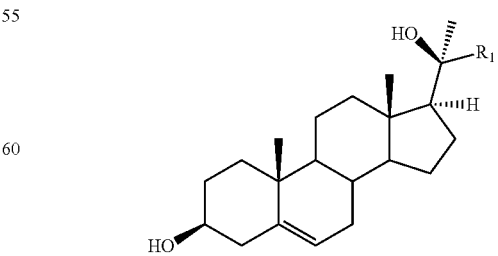

or a pharmaceutically acceptable salt, hydrate or solvate thereof, wherein R1 comprises an aliphatic or cyclic substituent having at least one carbon atom. In some embodiments, the active agent is a sterol comprising Oxy133.

In some embodiments, provided is an implant configured to fit at or near a bone defect to promote bone growth, the implant comprising: a biodegradable polymer in an amount of about 0.1 wt % to about 20 wt % of the implant and an oxysterol in an amount of about 20 wt % to about 90 wt % of the implant.

In some embodiments, provided is an implantable matrix configured to fit at or near a bone defect site to promote bone growth, the matrix comprising: a crosslinked biodegradable polymer in an amount of about 0.1 wt % to about 15 wt % of the matrix and an oxysterol in an amount of about 20 wt % to about 90 wt % of the matrix, the oxysterol having a concentration of about 100 mg/cc to about 1.0 g/cc.

In some embodiments, provided is a method for making an implant, the method comprising adding an oxysterol in an amount of about 20 wt % to about 90 wt % based on a total weight of the implant to a biodegradable polymer, the biodegradable polymer being in an amount of about 0.1 wt % to about 20 wt % based on the total weight of the implant to form the implant.

Additional features and advantages of various embodiments will be set forth in part in the description that follows, and in part will be apparent from the description, or may be learned by practice of various embodiments. The Objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

As shown in FIG. 2, the malleable implant is wetted with blood or bone marrow aspirate and formed into a cylindrical shape;

As shown in FIG. 3, the malleable implant is wetted with blood or bone marrow aspirate and formed into a spherical shape;

As shown in FIG. 4, the malleable implant is wetted with water or saline and formed into a cylindrical shape;

As shown in FIG. 5, the malleable implant is wetted with water or saline and formed into a spherical shape;

As shown in FIG. 6, implantation of the implants in the posterolateral space yielded spinal fusion in a rat two-level spine model. Bone growth in rat test subjects can be seen after 4 and 8 weeks post-implantation, and fusion was confirmed by manual palpation of the spine segments at 8 weeks; and FIG. 7 illustrates uses of a formulation of malleable implants having 125 mg of Oxy133 on each side of the implant, in accordance with the malleable implants described herein. As shown in FIG. 7, implantation of the implants in the posterolateral space yielded spinal fusion in a rat two-level spine model. Bone growth in rat test subjects can be seen after 4 and 8 weeks post-implantation, and fusion was confirmed by manual palpation of the spine segments at 8 weeks.

Figure 1:
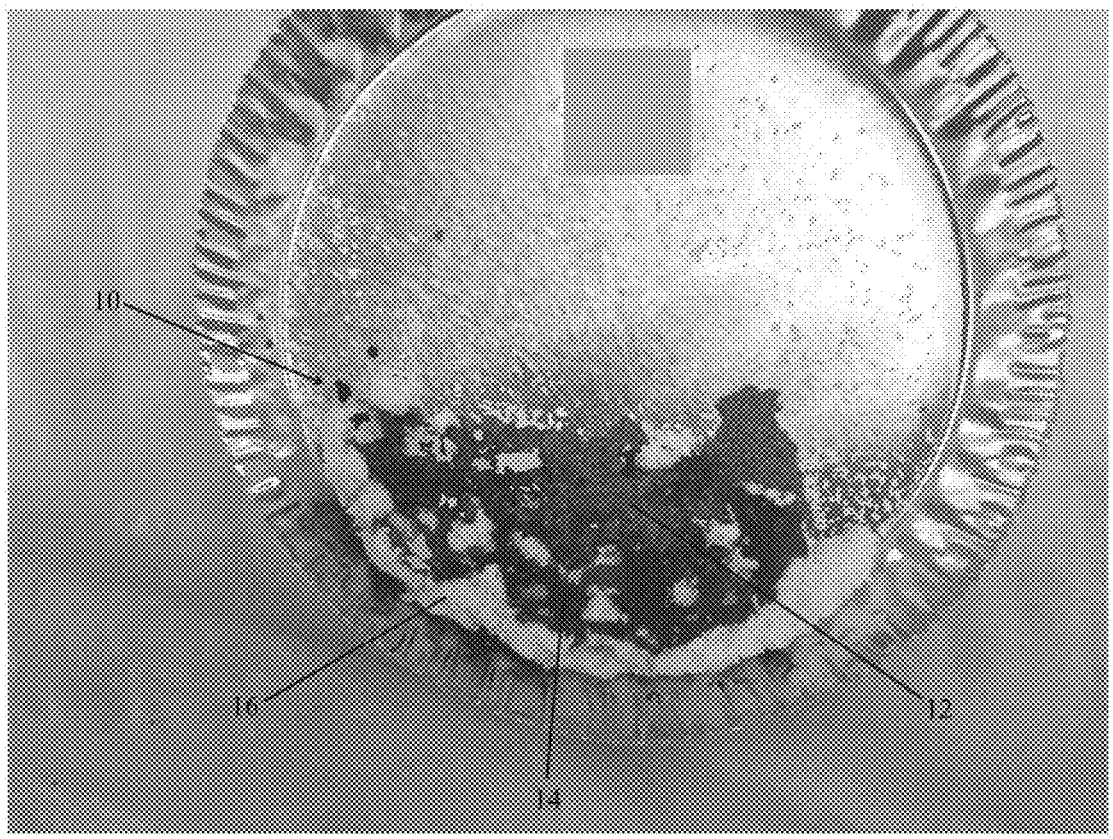
FIG. 1 illustrates powder components of a malleable implant which have been wetted by a fluid but have not yet been mixed. The cohesive mass includes a biodegradable polymer such as collagen, mineral particles such as ceramic, and an active agent such as an oxysterol.

It is to be understood that the figures may not be to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an implant" includes one, two, three or more implants.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug".

The term "biodegradable" includes compounds or components that will degrade over time by the action of enzymes, by hydrolytic action and/or by other similar mechanisms in the human body. In various embodiments, "biodegradable" includes that components can break down or degrade within the body to non-toxic components as cells (e.g., bone cells) infiltrate the components and allow repair of the defect. By "bioerodible" it is meant that the compounds or components will erode or degrade over time due, at least in part, to contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

The term "alkyl" as used herein, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkenyl." and/or "alkynyl" is used, as defined below. In some embodiments, the alkyl groups are (C1-C40) alkyl. In some embodiments, the alkyl groups are (C1-C6) alkyl.

The term "alkanyl" as used herein refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are (C1-C40) alkanyl. In some embodiments, the alkanyl groups are (C1-C6) alkanyl.

The term "alkenyl" as used herein refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is (C2-C40) alkenyl. In some embodiments, the alkenyl group is (C2-C6) alkenyl.

The term "alkynyl" as used herein refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc.; and the like. In some embodiments, the alkynyl group is (C2-C40) alkynyl. In some embodiments, the alkynyl group is (C2-C6) alkynyl.

The term "alkyldiyl" as used herein refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,2-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is (C1-C40) alkyldiyl. In some embodiments, the alkyldiyl group is (C1-C6) alkyldiyl. Also contemplated are saturated acyclic alkanyldiyl radicals in which the radical centers are at the terminal carbons, e.g., methandiyl (methano); ethan-1,2-diyl(ethano); propan-1,3-diyl(propano); butan-1,4-diyl(butano); and the like (also referred to as alkylenos, defined infra).

The term "alkyleno" as used herein refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In some embodiments, the alkyleno group is (C1-C40) alkyleno. In some embodiments, the alkyleno group is (C1-C6) alkyleno.

The terms "heteroalkyl," "heteroalkanyl," "heteroalkenyl," "heteroalkanyl," "heteroalkyldiyl" and "heteroalkyleno" as used herein refer to alkyl, alkanyl, alkenyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, —O—O—, —S—S—, —O—S—, —NR', =N—N=, —N=N—, —N(O)N—, —N=N—NR'—, —PH—, —P(O)2-, —O—P(O)2-, —SH2-, —S(O)2-, —SnH2- or the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

The term "aryl" as used herein refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is (C5-C14) aryl or a (C5-C10) aryl. Some preferred aryls are phenyl and naphthyl.

The term "aryldiyl" as used herein refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryldiyl group is (C5-C14) aryldiyl or (C5-C10) aryldiyl. For example, some preferred aryldiyl groups are divalent radicals derived from benzene and naphthalene, especially phena-1,4-diyl, naphtha-2,6-diyl and naphtha-2,7-diyl.

The term "arydeno" as used herein refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative doable bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure:

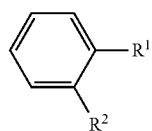

wherein $R^1$, when taken alone is hydrogen, or when taken together with $R^2$ is (C5-C14) aryleno; and $R^2$, when taken alone is hydrogen, or when taken together with $R^1$ is (C5-C14) aryleno.

When $R^1$ and $R^2$ are each hydrogen, the resultant compound is benzene. When $R^1$ taken together with $R^2$ is C6 aryleno (benzeno), the resultant compound is naphthalene. When $R^1$ taken together with $R^2$ is C10 aryleno (naphtaleno), the resultant compound is anthracene or phenanthrene. Typical aryleno groups include, but are not limited to, aceanthryleno, acenaphthyleno, acephenanthyleno, anthraceno, azuleno, benzeno (benzo), chryseno, coroneno, fluorantheno, fluoreno, hexaceno, hexapheno, hexyleno, asindaceno, s-indaceno, indeno, naphthalene (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, or the like. Where a specific connectivity is intended, the involved bridging carbon atoms (of the aryleno bridge) are denoted in brackets, e.g., [1,2]benzeno ([1,2]benzo), [1,2]naphthaleno, [2,3] naphthaleno, etc. Thus, in the above example, when $R^1$ taken together with $R^2$ is [2,3]naphthaleno, the resultant compound is anthracene. When $R^1$ taken together with $R^2$ is [1,2]naphthaleno, the resultant compound is phenanthrene. In a preferred embodiment, the aryleno group is (C5-C14), with (C5-C10) being even more preferred.

The term "arylaryl" as used herein refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. When the number of carbon atoms comprising an arylaryl group is specified, the numbers refer to the carbon atoms comprising each parent aromatic ring. For example, (C1-(14) arylaryl is an arylaryl group in which each aromatic ring comprises from 5 to 14 carbons, e.g., biphenyl, triphenyl, binaphthyl, phenylnaphthyl, etc. In some instances, each parent aromatic ring system of an arylaryl group is independently a (C5-C14) aromatic or a (C1-C10) aromatic. Some preferred are arylaryl groups in which all of the parent aromatic ring systems are identical, e.g., biphenyl, triphenyl, binaphthyl, trinaphthyl, etc.

The term "biaryl" as used herein refers to an arylaryl radical having two identical parent aromatic systems joined directly together by a single bond. Typical biaryl groups include, but are not limited to, biphenyl, binaphthyl, bianthracyl, and the like. In some instances, the aromatic ring systems are (C5-C14) aromatic rings or (C5-C10) aromatic rings. One preferred biaryl group is biphenyl.

The term "arylalkyl" as used herein refers to an acyclic alkyl radical in which one of the hydrogen atoms bonded to a carbon atom, typically a terminal or spa carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C6-C40) arylalkyl, e.g., the alkanyl, alkenyl or alkynyl moiety of the arylalkyl group is (C1-C26) and the aryl moiety is (C5-C14). In some preferred embodiments the arylalkyl group is (C6-C13), e.g., the alkanyl, alkenyl or alkynyl moiety of the arylalkyl group is (C1-C3) and the aryl moiety is (C5-C10).

The term "heteroaryl" as used herein refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindo line, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl, with 5-10 membered heteroaryl being particularly preferred. Some preferred heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryldiyl group is 5-14 membered heteroaryldiyl or a 5-10 membered heteroaryldiyl. Some preferred heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryleno" as used herein refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure:

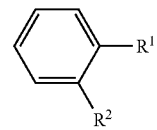

wherein $R^1$, when taken alone is hydrogen, or when taken together with $R^2$ is 5-14 membered heteroaryleno; and $R^2$, when taken alone is hydrogen, or when taken together with $R^1$ is 5-14 membered heteroaryleno;

When $R^1$ and $R^2$ are each hydrogen, the resultant compound is benzene. When R1 taken together with $R^2$ is a 6-membered heteroaryleno pyridino), the resultant compound is isoquinoline, quinoline or quinolizine. When $R^1$ taken together with $R^2$ is a 10-membered heteroaryleno (e.g., isoquinoline), the resultant compound is, e.g., acridine or phenanthridine. Typical heteroaryleno groups include, but are not limited to, acridino, carbazole, β-carbolino, chromeno, cinnolino, furan, imidazole, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridine, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, or the like. Where a specific connectivity is intended, the involved bridging atoms (of the heteroaryleno bridge) are denoted in brackets, e.g., [1,2] pyridino, [2,3]pyridino, [3,4]pyridino, etc. Thus, in the above example, when $R^1$ taken together with $R^2$ is [1,2] pyridino, the resultant compound is quinolizine. When $R^1$ taken together with R2 is [2,3]pyridino, the resultant compound is guillotine. When $R^1$ taken together with $R^2$ is [3,4]pyridino, the resultant compound is isoquinoline. In preferred embodiments, the heteroaryleno group is 5-14 membered heteroaryleno or 5-10 membered heteroaryleno. Some preferred heteroaryleno radicals are those derived from parent heteroaromatic ring systems in which any ring heteroatoms are nitrogens, such as imidazolo, indolo, indazolo, isoindolo, naphthyridino, pteridino, isoquinolino, phthalazino, purino, pyrazolo, pyrazino, pyridazino, pyndmo, pyrrolo, quinazolino, quinolino, etc.

The term "heteroaryl-heteroaryl" as used herein refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridyl-purinyl, bipurinyl, etc. When the number of ring atoms are specified, the numbers refer to the number of atoms comprising each parent heteroaromatic ring systems. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. In some embodiments, each parent heteroaromatic ring system is independently a 5-14 membered heteroaromatic, more preferably a 5-10 membered heteroaromatic. Also preferred are heteroaryl-heteroaryl groups in which all of the parent heteroaromatic ring systems are identical. Some preferred heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "biheteroaryl" as used herein refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-14 membered heteroaromatic rings or 5-10 membered heteroaromatic rings. Some preferred biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

The term "heteroarylalkyl" as used herein refers to an acyclic alkyl radical in which one of the hydrogen atoms bonded to a carbon atom, typically a terminal or sp2 carbon atom, is replaced with a heteroaryl radical. Where specific alkyl moieties are intended, the nomenclature heteroarylalkanyl, heteroarylakenyl and/or heterorylalkynyl is used. In some embodiments, the heteroarylalkyl group is a 6-20 membered heteroarylalkyl, e.g., the alkanyl, alkenyl or alkanyl moiety of the heteroarylalkyl is 1-6 membered and the heteroaryl moiety is a 5-14-membered heteroaryl. In some preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

The term "substituted" as used herein refers to a radical in which one or more hydrogen atoms are each independently replaced with the same or different substituent(s). Typical substituents include, but are not limited to, —X—, —R, —O—, =O, —OR, —O—OR, —SR, —S—, =S, —NRR, =NR, perhalo (C1-C6) alkyl, —CX3, —CF3, —CN, —OCN, —SCN, —NCO, —NCS, —NO, —NO2, =N2, —N3, —S(O)2O—, —S(O)2OH, —S(O)2R, —C(O)R, —C(O)X, —C(S)R, —C(S)X, —C(O)OR, —C(O)O—, —C(S)OR, —C(O)SR, —C(S)SR, —C(O)NRR, —C(S)NRR and —C(NR)NRR, where each X is independently a halogen (e.g., —F or —Cl) and each R is independently hydrogen, alkyl, alkanyl, alkenyl, alkanyl, aryl, arylalkyl, arylaryl, heteroaryl, heteroarylalkyl or heteroaryl-heteroaryl, as defined herein. The actual substituent substituting any particular group will depend upon the identity of the group being substituted.

The term "solvate" as used herein refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compound of the disclosure may merely retain adventitious water or be a mixture of water plus some adventitious solvent.

The term "oxysterol" as used herein is meant to encompass one or more forms of oxidized cholesterol. The oxysterols described herein are either independently or collectively active to bone growth in a patient, as described in WO 2013169399 A1, which is hereby incorporated by reference in its entirety.

The oxysterol can be in a pharmaceutically acceptable salt. Some examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloride, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Pharmaceutically acceptable salts of oxysterol include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amities including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

In some embodiments, in order to reduce the solubility of the oxysterol to assist in obtaining a controlled release depot effect, the oxysterol is utilized as the free base or utilized in a salt which has relatively lower solubility. For example, the present application can utilize an insoluble salt such as a fatty acid salt. Representative fatty acid salts include salts of oleic acid, linoleic acid, or fatty acid salts with between 8 to 20 carbons solubility, such as for example, palmeate or stearate.

The terms "bioactive" composition or "pharmaceutical" composition as used herein may be used interchangeably. Both terms refer to compositions that can be administered to a subject. Bioactive or pharmaceutical compositions are sometimes referred to herein as "pharmaceutical compositions" or "bioactive compositions" of the current disclosure. Sometimes the phrase "administration of Oxy133" is used herein in the context of administration of this compound to a subject (e.g., contacting the subject with the compound, injecting the compound, administering the compound in an implant, etc.). It is to be understood that the compound for such a use can generally be in the form of a pharmaceutical composition or bioactive composition comprising the oxysterol (e.g., Oxy133).

A "therapeutically effective amount" or "effective amount" is such that when administered, the oxysterol (e.g., Oxy133) results in alteration of the biological activity, such as, for example, enhancing bone growth, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In some embodiments, the matrix can be a biodegradable depot.

The term "implantable" as utilized herein refers to a biocompatible device (e.g., implant) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a bone cavity, or in close proximity (within about 0.1 cm, or preferably within about 10 cm, for example) thereto. For example, the oxysterol dose delivered locally from the implant may be, for example, 10%, 20%, 30%, 40%, 50%, 60%, 70%, 80%, 90%, 95%, 99%, 99.9% or 99.999% less than the oral dosage or injectable dose.

The term "mammal" refers to organisms from the taxonomy class "mammalian," including but not limited to humans, other primates such as monkeys, chimpanzees, apes, orangutans and monkeys, rats, mice, rabbits, cats, dogs, pigs, cows, horses, etc.

The term "particle" refers to pieces of a substance of all shapes, sizes, thickness and configuration such as fibers, threads, narrow strips, thin sheets, clips, shards, etc., that possess regular, irregular or random geometries. It should be understood that some variation in dimension will occur in the production of the particles and particles demonstrating such variability in dimensions are within the scope of the present application. For example, the mineral particles (e.g., ceramic) can be from about 0.5 mm to about 1.5 mm. In some embodiments, the mineral particles can be from about 0.2 mm to about 0.5 mm.

In some embodiments, the medical device comprises a matrix. The "matrix" of the present application is utilized as a scaffold for bone and/or cartilage repair, regeneration, and/or augmentation. Typically, the matrix provides a 3-D matrix of interconnecting pores, which acts as a scaffold for cell migration. The morphology of the matrix guides cell migration and cells are able to migrate into or over the matrix, respectively. The cells then are able to proliferate and synthesize new tissue and form bone and/or cartilage. In some embodiments, the matrix is resorbable.

In some embodiments, the matrix can be malleable, cohesive, flowable and/or can be shaped into any shape. The term "malleable" includes that the matrix is capable of being converted from a first shape to a second shape by the application of pressure.

The term "cohesive" as used herein means that the putty tends to remain a singular, connected mass upon movement, including the exhibition of the ability to elongate substantially without breaking upon stretching.

The term "moldable" includes that the matrix can be shaped by hand or machine or injected in the target tissue site (e.g., bone defect, fracture, or void) in to a wide variety of configurations. In some embodiments, the matrix can be formed into sheets, blocks, rings, struts, plates, disks, cones, pins, screws, tubes, teeth, bones, portion of bone, wedges, cylinders, threaded cylinders, or the like, as well as more complex geometric configurations.

The oxysterol can be "osteogenic," where it can enhance or accelerate the ingrowth of new bone tissue.

New compositions and methods are provided for implantable malleable osteogenic medical material comprising a combination of a biodegradable polymer, mineral particles and an active agent comprising an oxysterol.

The section headings below should not be restricted and can be interchanged with other section headings.

Oxysterols

In some embodiments, the malleable implant can be a robust implant that can have a high mineral content or allograft content, still bind and be cohesive. In some embodiments, there is a malleable implant configured to fit at or near a bone defect to promote bone growth, the malleable implant comprising: a biodegradable polymer in an amount of about 0.1 wt % to about 20 wt % of the implant, mineral particles in an amount of about 0.1 wt % to about 95 wt % of the implant, and an oxysterol, the implant configured to become moldable upon being wetted with a fluid.

Oxysterols are a family of molecules consisting of oxygenated derivatives of cholesterol. Oxysterols are involved in many biological processes, and have been found to possess osteogenic properties. For example, one naturally occurring oxysterol, 20(S)-hydroxycholesterol, has osteogenic and anti-adipogenic properties. Such oxysterols can be useful in healing bone fractures, long bone fusion procedures, spinal fusion procedures, interbody spinal fusion procedures, posterolateral spinal fusion procedures, cervical discectomy and fusion procedures, dental procedures, and cranial/maxillofacial procedures.

Oxysterols also play a role in various physiological processes, such as cellular differentiation, inflammation, apoptosis, and steroid production. Oxysterols are products of cholesterol oxidation and are formed in vivo by a variety of cell types including osteoblasts (Schroepfer. *Phyiol Rev* 80:361-554, 2000; Bjorkhem and Dicsfalusy. *Arterioscler*

Thromb Vase Biol 22:734-742, 2002). Certain oxysterols, such as 20(S)-hydroxycholesterol, as well as 22(S)- or 22(R)-hydroxycholesterol, induce osteogenic differentiation in multipotent mesenchymal cells such as M2-10B4 (M2) marrow stromal cells and C3H10T1/2 embryonic fibroblasts (Kha et al. *J Bone Miner Res* 19:830-840, 2004). Oxysterols can induce osteogenic and inhibit adipogenic differentiation of mesenchymal stem cells through activation of the hedgehog signaling pathway, which in turn regulates the master switches that control osteogenic and adipogenic differentiation, namely Runx2 and PPARγ, respectively (Richardson et al. *J Cell Biochem* 100:1131-1145, 2007; Dwyer et al. *J Biol Chem* 282: 8959-8968, 2007; Kim et al., *J Bone Miner Res* 22:1711-1719, 2007). Some oxysterols also provide therapeutic uses for treatment of bone defects or disorders such as osteoporosis.

The implants described herein can be useful in creating new therapeutic implants and matrices that include an oxysterol for induction of local bone formation and treatment of bone defects. The oxysterol is retained in the matrix and released over time, while the matrix allows influx of bone cells to grow bone and fill the defect. In some embodiments, such applications are based on the ability of these oxysterol compounds to induce the hedgehog signaling pathway. In some embodiments, the implant causes mesenchymal stem cells to show induced expression of markers of osteoblast differentiation. The implants and matrices described herein can be used for a variety of therapeutic uses including but not limited to induction of local bone formation and treatment of bone defects. In some embodiments, implants containing oxysterol as described herein induce a biological response when the implant contacts a human or animal cell. In some embodiments, the cell can be a mesenchymal stem cell or a bone marrow stromal cell. In some embodiments, the biological response comprises stimulating osteoblastic differentiation, inhibiting adipocyte differentiation, or stimulating cartilage formation. In some embodiments, the implant is configured as an implant to release the oxysterol to induce a biological response at or near a surgical site or a bone defect site.

Oxysterols can be used to induce systemic bone formation to treat bone defects such as osteoporosis, to induce local bone formation to treat conditions such as nonunion fractures, or other bone disorders, such as jaw bone defects in dental applications/implants, and to induce spinal fusion. In some embodiments, the implant may include an oxysterol alone or in combination with one or more bone morphogenetic proteins or osteogenic agents. In some embodiments, more than one oxysterol is present in the implant. In some embodiments, the implants include Oxy133 and/or Oxy153.

In some embodiments, the implant or matrix includes oxysterols which aid in osteogenesis. In some embodiments, the implant or matrix includes Oxy34, Oxy49, and/or Oxy133. In some embodiments, the implant or matrix includes an oxysterol comprising the structure:

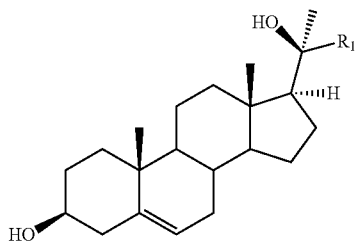

or a pharmaceutically acceptable salt, hydrate or solvate thereof, wherein R1 comprises an aliphatic or cyclic substituent having at least one carbon atom.

In some embodiments, R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroarylheteroaryl, a biheteroaryl, a heteroarylalkyl or combinations thereof. In some embodiments, the R substituent comprises a (C1-C20) alkyl or heteroalkyl, a ($C_2$-$C_{20}$) aryl or heteroaryl, a ($C_6$-$C_{26}$) arylalkyl or heteroalkyl and a ($C_5$-C20) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

The present disclosure includes an implant or matrix including an osteogenic oxysterol (e.g., Oxy133) and its ability to promote osteogenic differentiation in vitro. Oxy133 is a particularly effective osteogenic agent. In various applications, Oxy133 is useful in treating conditions that would benefit from localized stimulation of bone formation, such as, for example, spinal fusion, fracture repair, bone regenerative/tissue applications, augmentation of bone density in the jaw for dental implants, osteoporosis or the like. One particular advantage of Oxy133 is that it provides greater ease of synthesis and improved time to fusion when compared to other osteogenic oxysterols. Oxy133 is a small molecule that can serve as an anabolic therapeutic agent for bone growth, as well as a useful agent for treatment of a variety of other conditions.

One aspect of the application disclosure is an implant or a matrix including Oxy133, having the formula:

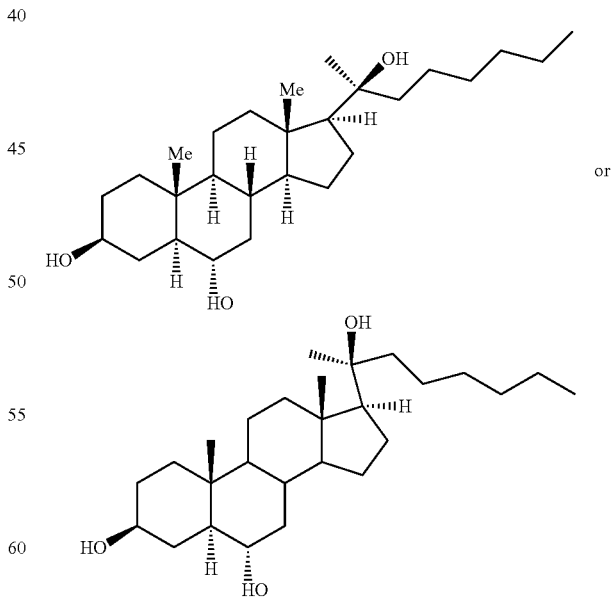

or a pharmaceutically acceptable salt, solvate or hydrate thereof. The Oxy133 may be used as a bioactive or pharmaceutical composition comprising Oxy133 or a pharmaceutically acceptable salt, solvate or hydrate thereof and a pharmaceutically acceptable carrier. Oxy133 has the IUPAC designation (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol.

Another aspect of the disclosure is a method for inducing (stimulating, enhancing) a hedgehog (Hh) pathway mediated response, in a cell or tissue, comprising contacting the cell or tissue with a therapeutically effective amount of Oxy133. The cell or tissue can be in vitro or in a subject, such as a mammal. The hedgehog (Hh) pathway mediated response involves the stimulation of osteoblastic differentiation, osteomorphogenesis, and/or osteoproliferation; the stimulation of hair growth and/or cartilage formation; the stimulation of neovasculogenesis, e.g., angiogenesis, thereby enhancing blood supply to ischemic tissues; or it is the inhibition of adipocyte differentiation, adipocyte morphogenesis, and/or adipocyte proliferation; or the stimulation of progenitor cells to undergo neurogenesis. The Hh mediated response can comprise the regeneration of any of a variety of types of tissues, for use in regenerative medicine. Another aspect of the disclosure is a method for treating a subject having a bone disorder, osteopenia, osteoporosis, or a bone fracture, comprising administering to the subject an effective amount of a bioactive composition or pharmaceutical composition comprising Oxy133. The subject can be administered the bioactive composition or pharmaceutical composition at a therapeutically effective dose in an effective dosage form at a selected interval to, e.g., increase bone mass, ameliorate symptoms of osteoporosis, reduce, eliminate, prevent or treat atherosclerotic lesions, or the like. The subject can be administered the bioactive composition or pharmaceutical composition at a therapeutically effective dose in an effective dosage form at a selected interval to ameliorate the symptoms of osteoporosis. In some embodiments, a composition comprising Oxy133 may include mesenchymal stem cells to induce osteoblastic differentiation of the cells at a targeted surgical area.

In various aspects, the Oxy133 can be administered to a cell, tissue or organ by local administration. For example, the Oxy133 can be applied locally with a cream or the like, or it can be injected or otherwise introduced directly into a cell, tissue or organ, or it can be introduced with a suitable medical device, such as an implant as discussed herein.

In some embodiments, the dosage of Oxy133 is from approximately 10 pg/day to approximately 80 g/day. In some embodiments, the dosage of Oxy133 is from approximately 1.0 g/day, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60.0 grams/day. Additional dosages of Oxy133 include from approximately 2.4 ng/day to approximately 50 mg/day; approximately 50 ng/day to approximately 2.5 mg/day; approximately 250 ng/day to approximately 250 mcg/day; approximately 250 ng/day to approximately 50 mcg/day; approximately 250 ng/day to approximately 25 mcg/day; approximately 250 ng/day to approximately 1 mcg/day; approximately 300 ng/day to approximately 750 ng/day or approximately 0.50 mcg/day to 500 ng/day. In various embodiments, the dose may be about 0.01 to approximately 10 mcg/day or approximately 1 ng/day to about 120 mcg/day. In some embodiments, the dosage of Oxy133 is in greater amounts. For example, in some embodiments, the dosage of Oxy133 is from 0.01 mg/day to 5 g/day.

The matrix can comprise the oxysterol (e.g., Oxy133) disposed homogenously throughout it or in discrete regions or discrete layers of the matrix. The oxysterol can be loaded in the matrix and can comprise from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60% w/v, w/w and/or v/v of the total weight of the matrix.

In some embodiments, a high concentration of the oxysterol can be loaded into the matrix and comprises from about 20 wt % to about 99 wt % of the matrix. In some embodiments, the oxysterol can be loaded into the matrix in an amount from about 20 wt % to about 90 wt %, 35 wt % to about 80 wt % or about 50 wt % to about 90 wt % of the matrix. In some embodiments, the oxysterol can be loaded into the matrix in an amount of about 20 wt % to about 30 wt about 30 wt % to about 40 wt %, about 40 wt % to about 50 wt %, about 50 wt % to about 60 wt %, about 60 wt % to about 70 wt %, about 70 wt % to about 80 wt %, about 80 wt % to about 90 wt %, or about 90 wt % to about 99 wt %. In some embodiments, the oxysterol can be loaded into the matrix in an amount of from about 20, 25, 30, 35, 40, 45, 50, 55, 60, 65, 70, 75, 80, 85, 90, 95, to about 99 wt % of the matrix.

The oxysterol can be loaded in the matrix and can comprise from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60 mg/cc of the matrix. In some embodiments, the oxysterol can be loaded into the matrix in an amount of about 400 mg/cc. In some embodiments, the oxysterol can be loaded into the matrix in an amount of about 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to about 500 mg/cc. In some embodiments, 400 mg/cc can be loaded in the matrix.

In some embodiments, the oxysterol can be loaded to the matrix in highly concentrated amounts. For example, in some embodiments, the oxysterol is loaded into the matrix in an amount of at least 500 mg/cc. In some embodiments, the oxysterol is added to the matrix in an amount of about 1 mg/cc to about 1 g/cc, from about 100 mg/cc to about 1 g/cc, from about 500 mg/cc to about 900 mg/cc, or from about 600 mg/cc to about 800 mg/cc. In other embodiments, the oxysterol is added to the matrix in an amount of about 500 mg/cc to about 600 mg/cc, about 600 mg/cc to about 700 mg/cc, about 700 mg/cc to about 800 mg/cc, about 800 mg/cc to about 900 mg/cc, or about 900 mg/cc to about 1 g/cc.

In addition to the compound Oxy133, other embodiments of the disclosure encompass any and all individual stereoisomers at any of the stereocenters present in Oxy133, including diastereomers, racemates, enantiomers, and other isomers of the compound, in embodiments of the disclosure, Oxy133 may include all polymorphs, solvates or hydrates of the compound, such as hydrates and those formed with organic solvents.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts. Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

In various embodiments, Oxy133 includes one or more biological frictions. That is, Oxy133 can induce a biological response when contacted with a mesenchymal stem cell or a bone marrow stromal cell. For example, Oxy133 may stimulate osteoblastic differentiation. In some embodiments, a bioactive composition including Oxy133 may include one or more biological functions when administered to a mammalian cell, for example, a cell in vitro or a cell in a human or an animal. For example, such a bioactive composition may stimulate osteoblastic differentiation. In some embodiments, such a biological function can arise from stimulation of the hedgehog pathway.

Purification of Oxy133

In some embodiments, the oxysterol, for example Oxy133, is highly purified. In some embodiments, the Oxy133 may be crystallized or recrystallized. In some embodiments, purified Oxy133 is formed by recrystallizing Oxy133 in a 3:1 mixture of acetone/water, as shown below:

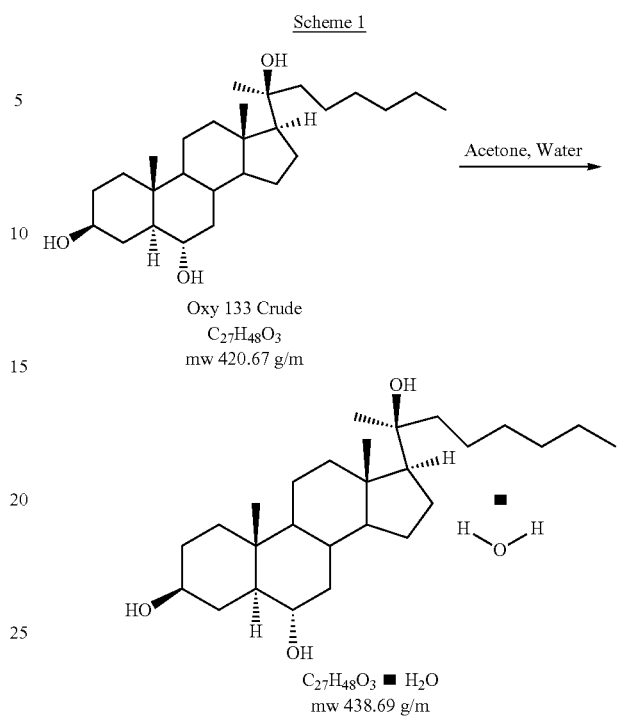

Scheme 1

Oxy 133 Crude
$C_{27}H_{48}O_3$
mw 420.67 g/m $C_{27}H_{48}O_3 \cdot H_2O$
mw 438.69 g/m As shown above, upon crystallization, the purified Oxy133 forms a hydrate. However, in some embodiments, the Oxy133 is in the anhydrous form. In some embodiments, the percent crystallinity of any of the crystalline forms of Oxy133 described herein can vary with respect to the total amount of Oxy133.

In certain embodiments the Oxy133 can have a percent crystallinity of a salt, hydrate, solvate or crystalline form of Oxy133 to be at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of Oxy133 appears to be crystalline as best can be determined using methods known in the art. Accordingly, therapeutically effective amounts of Oxy133 can include amounts that vary in crystallinity. These include instances where an amount of the crystallized Oxy133 in a solid form is subsequently dissolved, partially dissolved, or suspended or dispersed in a liquid.

In one embodiment, the purified Oxy133 is crystallized as a monohydrate. However, in other embodiments the purified Oxy133 may be crystallized in other hydrous forms, such as, for example, a dihydrate, a hemihydrate, a sesquihydrate, a trihydrate, a tetrahydrate and the like, as well as the corresponding solvated forms. In some embodiments, the Oxy133 is crystallized in an amorphous form. In other embodiments, the purified Oxy133 is crystallized as a co-crystal or a pharmaceutically acceptable salt.

In some embodiments, the oxysterol (e.g., Oxy133) that can be used can be in amorphous form and have faster dissolution and release from the matrix. Such as, for example, a burst release from the matrix of from about 10%, 15%, 20%, 25%, 30%, 35%, 45%, to about 50% of the oxysterol over 24 or 48 hours.

In some embodiments, the unpurified Oxy133 may be solidified by mixing with heptanes. The product may be subsequently filtered and suspended in methylene chloride. In some embodiments, the unpurified Oxy133 may be filtered from the suspension and crystallized with the use of acetone and water or other organic or inorganic solvents (e.g., diethyl ether, dichloromethane, ethyl acetate, acetone, n,n-dimethylformamide, acetonitrile, dimethyl sulfoxide, ammonia, t-butanol, n-propanol, ethanol, methanol, acetic acid or a combination thereof).

In various embodiments, the unpurified Oxy133 may be isolated and purified by any other traditional means. That is, the unpurified Oxy133 can be isolated and purified to the desired purity, e.g., from about 95% to about 99.9% by filtration, centrifugation, distillation to separate volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods.

In some embodiments, the purified Oxy133 is formed in crystal form via crystallization, which separates the Oxy133 from the liquid feed stream by cooling the liquid feed stream or adding precipitants which lower the solubility of byproducts and unused reactants in the reaction mixture so that the Oxy133 forms crystals. In some embodiments, the solid crystals are then separated from the remaining liquor by filtration or centrifugation. The crystals can be resolubilized in a solvent and then recrystallized and the crystals are then separated from the remaining liquor by filtration or centrifugation to obtain a highly pure sample of Oxy133. In some embodiments, the crystals can then be granulated to the desired particle size. For example, the mineral particles (e.g., ceramic) can be from about 0.5 mm to about 1.5 mm. In some embodiments, the mineral particles can be from about 0.2 mm to about 0.5 mm.

In some embodiments, the unpurified Oxy133 can be purified where the purified Oxy133 is formed in crystallized form in a solvent and then removed from the solvent to form a high purity Oxy133 having a purity of from about 98% to about 99.99%. In some embodiments, the Oxy133 can be recovered via filtration or vacuum filtration before or after purification.

Implants and Uses

In some embodiments, the implant comprises a matrix that provides a tissue scaffold for cells to guide the process of tissue formation in vivo in three dimensions. In some embodiments, the implant provides a porous scaffold to promote bone ingrowth. The morphology of the matrix guides cell migration and cells are able to migrate into or over the matrix. The cells then are able to proliferate and synthesize new tissue and form bone and/or cartilage. In some embodiments, one or more tissue matrices are stacked on one another.

In some embodiments, the implant is in a dry cohesive mass. In some embodiments, the implant comprises a cohesive mass of a biodegradable polymer, mineral particles and an oxysterol. The biodegradable polymer, mineral particles and oxysterol comprise fibers, chips or particles which form a coherent mass without any additional carrier. In some embodiments, the fibers, chips or particles are processed in such a way to provide for cohesion between biodegradable polymer, mineral particles and an oxysterol without additional containment or binding agents. In some embodiments, for example, the biodegradable polymer may be milled to create curled fibers. The fibers and particles become physically entangled by surface to surface interactions between adjacent fibers, chips and/or particles. In some embodiments, the entanglement/interaction of the fibers, chips and/or particles is responsible for the cohesiveness of the implant prior to being wetted with a fluid. Thus, in some embodiments, the implant comprises fibers, chips and/or particles having a size and shape that provides for increased surface area and the ability to mechanically interlock with one another to form a coherent mass.

In some embodiments, the implant is a dry mass of a biodegradable polymer, mineral particles and an oxysterol. Each of the biodegradable polymer, mineral particles and an oxysterol comprises particles which are homogenously mixed with each other. As shown in FIG. 1, the powder components of matrix 10 comprise at least three components that have been wetted with a fluid. In some embodiments, matrix 10 comprises a biodegradable polymer 12, mineral particles 14 and an oxysterol 16. In some embodiments, the matrix also comprises an expandable phase, such as, for example, carboxymethylcellulose or other cellulose derivatives. As shown in FIG. 1 the matrix exists as a mixture of particles which may be mechanically hound to one another to improve holding properties. In some embodiments, the biodegradable polymer 12, mineral particles 14 and oxysterol 16 are homogenously dispersed so that once the matrix is wetted, the implant will have uniform properties throughout.

The dried implant material comprises a porous body that includes a particulate mineral material having an average particle diameter of about 0.4 mm to about 5.0 mm homogenously mixed with a biodegradable polymer. In some embodiments, the mineral particles have an average particle size of about 0.5 mm to about 1.5 mm. In some embodiments, the mineral particles have an average particle size of about 125 micrometers to about 750 micrometers.

In some embodiment, the particulate minerals (e.g., TCP: HA) can be homogenously disposed throughout the matrix at a particle size of from about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 071, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1.0, 1.25, 1.4, 1.5, 1.6, 1.7, 1.8, 1.9, 2.0, 2.25 to about 2.5 mm. These particles can be in the form of granules, chips, fibers or a combination thereof.

In various embodiments, the particle size distribution of the biodegradable polymer may be about 10 micrometers, 13 micrometers, 85 micrometers, 1100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

In some embodiments, the one or more oxysterols may for example have an average particle size of from about 2.2 to about 10 microns. In some embodiments the oxysterol particles have a minimum average particle size of about 2.2 microns, or about 2.5 microns, or about 3 microns, or about 4 microns. The particles also may have a maximum average particle size of about 10 microns, or about 8 microns, or about 7 microns, or about 5 microns. In some embodiments, the oxysterol has a particle size from about 5 to 30 micrometers, or about 2 microns to about 20 microns, or from 30 microns to 100 microns, however, in various embodiments, ranges from about 1 micron to 250 microns may be used. In some embodiments, the oxysterol has a particle size of about 0.1 nm to about 1 micron to provide enhanced dissolution and quicker release of from the implant. In some embodiments, the oxysterol (e.g., Oxy133) is in nanoparticle form and from about 10.0, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to about 500 nm in diameter.

In some embodiments, the oxysterol includes a particle size of about 0.1 nm to about 5 mm to lengthen the release duration from the implant by slowing down Oxy133 dissolution rate which might modulate bone formation. Moreover, the oxysterol particles may have a monophasic distribution. Additionally, in some embodiments, it may be preferable to have a water-soluble oxysterol in order to produce an acute anti-inflammatory/analgesic effect that the implant is not providing.

In various embodiments, the oxysterol is in the form of a solvate, hydrate or a pharmaceutically acceptable salt. The oxysterol may alternatively be crystallized in an amorphous form. In some embodiments, the oxysterol is in the form of a monohydrate. In some embodiments, the oxysterol (e.g., Oxy133) may be in amorphous form. In various embodiments, the implant comprises Oxy133 and a biodegradable polymer in amorphous, crystalline or semicrystalline form; where the crystalline form may include polymorphs, solvates or hydrates.

In some embodiments, a matrix of the present application includes an oxysterol in an amount from about mg/cc to about 500 mg/cc. The matrix may include the oxysterol in an amount of from about 10 mg/cc, 20 mg/cc, 25 mg/cc, 30 mg/cc, 40 mg/cc, 50 mg/cc, 60 mg/cc, 70 mg/cc, 80 mg/cc, 90 mg/cc, 100 mg/cc, 110 mg/cc, 120 mg/cc, 130 mg/cc, 140 mg/cc, 150 mg/cc, 160 mg/cc, 170 mg/cc, 180 mg/cc, 190 mg/cc, 200 mg/cc, 210 mg/cc, 220 mg/cc, 230 mg/cc, 240 mg/cc, 250 mg/cc, 260 mg/cc, 270 mg/cc, 280 mg/cc, 290 mg/cc, 300 mg/cc, 310 mg/cc, 320 mg/cc, 330 mg/cc, 340 mg/cc, 350 mg/cc, 360 mg/cc, 370 mg/cc, 380 mg/cc, 390 mg/cc, 400 mg/cc, 410 mg/cc, 420 mg/cc, 430 mg/cc, 440 mg/cc, 450 mg/cc, 460 mg/cc, 470 mg/cc, 480 mg/cc, 490 mg/cc, to about 500 mg/cc or any amount therebetween. In some embodiments, the matrix releases 40 ng to about 5 mg of the oxysterol every hour.

In some embodiments, the oxysterol can be loaded to the matrix in highly concentrated amounts. For example, in some embodiments, the oxysterol is loaded into the matrix in an amount of at least 500 mg/cc. In some embodiments, the oxysterol is added to the matrix in an amount of about 1 mg/cc to about 1 g/cc, from about 100 mg/cc to about 1 g/cc, from about 500 mg/cc to about 900 mg/cc, or from about 600 mg/cc to about 800 mg/cc. In other embodiments, the oxysterol is added to the matrix in an amount of about 500 mg/cc to about 600 mg/cc, about 600 mg/cc to about 700 mg/cc, about 700 mg/cc to about 800 mg/cc, about 800 mg/cc to about 900 mg/cc, or about 900 mg/cc to about 1 g/cc. In some embodiments, the oxysterol is loaded into the matrix in an amount of about 134 mg/cc.

In some embodiments, the oxysterol comprises a range of about 5.0 wt % to about 45 wt % based on the total weight of the matrix or the implant prior to or after being wetted. In some embodiments, the implant comprises at least one biodegradable material in a wt % of about 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, or 44% based on the total weight of the matrix or the implant.

In some embodiments, the matrix containing the oxysterol may have a burst release surface that releases about 10%, 15%, 20%, 25%, 30%, 35%, 45%, to about 50% of the oxysterol over 24 or 48 hours.

In some embodiments, a high concentration of the oxysterol can be loaded into the matrix and comprise from about 20 wt % to about 90 wt % of the matrix. In some embodiments, the oxysterol can be loaded into the matrix in an amount from about 35 wt % to about 80 wt % or about 50 wt % to about 90 wt % of the matrix. In some embodiments, the oxysterol can be loaded into the matrix in an amount of about 20 wt % to about 30 wt %, about 30 wi % to about 40 wt %, about 40 wi % to about 50 wt %, about 50 wt % to about 60 wt %, about 60 wt % to about 70 wt %, about 70 wt % to about 80 wt %, about 80 wt % to about 90 wt %, or about 90 wt % to about 99 wt %. In some embodiments, the oxysterol can be loaded into the matrix in an amount of 20, 25, 30, 35, 40, 45, 50, 55, 60, 65, 70, 75, 80, 85, 90, or 95 wt % of the matrix.

In some embodiments, the matrix releases the oxysterol over a period of 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days. 3 days to 135 days, 3 days to 180 days, or 3 days to 6 months. In some embodiments, bone growth will be observed over a period of at least 14 days, for example, 14-90 days, 14-30 days, 14-60 days, 21-90 days, 21-180 days; 14-210 days, or 14 days to 6 months.

In some embodiments, the one or more biodegradable polymers (e.g., collagen) comprises 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0% w/v or v/v of the matrix. In some embodiments, the biodegradable polymer is present in an amount of about 0.1 wt % to about 20 wt % of the matrix. In some embodiments, the biodegradable polymer is present in an amount between about 0.01 wt % to about 50 wt %, about 8.0 wt % to about 20 wt % or about 8.0 wt % to about 13 wt % of the matrix. In some embodiments, the biodegradable polymer is present in an amount of about 0.1 wt % to about 10 wt %, about 10 wt % to about 20 wt %, about 20 wt % to about 30 wt %, about 30 wt % to about 40 wt %, or about 40 wt % to about 50 wt %.

In some embodiments, the implant is wetted to form a malleable matrix. The malleable matrix is configured to be moldable to any desired shape to fit a bone defect site. In some embodiments, the malleable implant may be molded to fit into a surgical site, such as a bone defect site. The shape of the matrix may be tailored to the site at which it is to be situated. For example, it may be in the shape of a morsel, a plug, a pin, a peg, a cylinder, a block, a wedge, a sheet, a strip, etc. The term "shape" refers to a determined or regular form or configuration in contrast to an indeterminate or vague form or configuration (as in the case of a lump or other solid mass of no special form) and is characteristic of such materials as sheets, plates, disks, cores, tubes, wedges, cylinders, or the like. This includes forms ranging from regular, geometric shapes to irregular, angled, or nongeometric shapes, or combinations of features having any of these characteristics. In some embodiments, the implant is malleable prior to being implanted into a surgical site. In such embodiments, a medical practitioner may mold the implant to a desired shape and allow the implant to cure or dry prior to implantation. In some embodiments, the implant is malleable in vivo. In such embodiments, a medical practitioner may mold the implant directly into a bone defect site. The implant is malleable and configured to be pressed into a bone defect site to fill out all crevices in a bone defect site. In some embodiments, the implant is malleable when wetted and is configured to remain malleable while in contact with a bone defect site.

In some embodiments, the malleable matrix can be formed to fit into the void space of an interbody cage or around the outside of the cage in the intervertebral space.

The dry, coherent mass may be wetted or hydrated with a variety of fluids to form a malleable and moldable implant. In some embodiments, the matrix is wetted with sterile water, physiological saline, sodium chloride, dextrose, Lactated Ringer's solution, PBS, blood, bone marrow aspirate, bone marrow fractions or a combination thereof. The amount of fluid that the matrix can be wetted with includes from about 0.25, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 to about 50.0 mls.

In some embodiments, the bone repair composition is hydrated with hyaluronic acid, cellulose ethers (such as carboxymethyl cellulose), collagen, gelatin, autoclaved bone powder, osteoconductive carriers, whole blood, blood fractions, bone marrow aspirate, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma. After hydrating, the bone repair composition becomes a putty or a paste that can be molded into a predetermined shape or administered to a bone defect and manipulated to conform to the bone defect in such a manner that will promote healing. For example, the composition may be hydrated with about 2 ml of saline blood per 2.5 g of combined DBM and periosteal powder.

Figure 2:
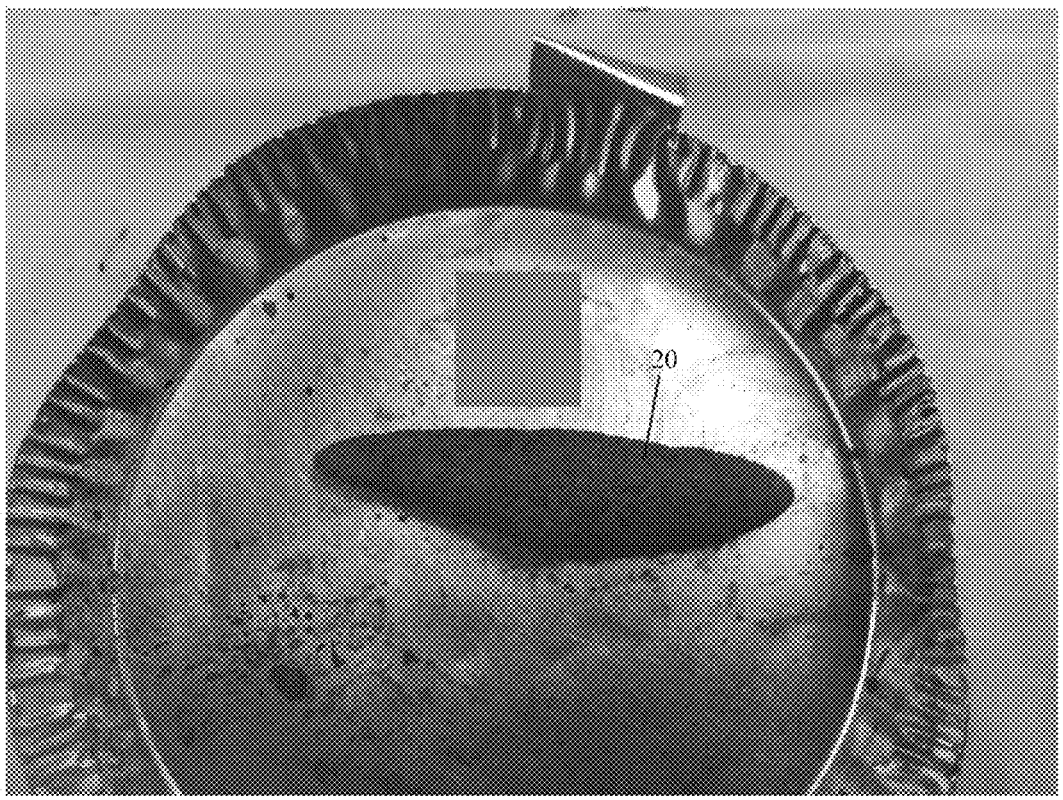
FIG. 2 illustrates a malleable implant after it has been wetted by a fluid. The malleable implant includes a biodegradable polymer such as collagen, mineral particles such as ceramic, and an active agent such as an oxysterol. The malleable implant is moldable into a shape to fit a bone defect.
Figure 3:
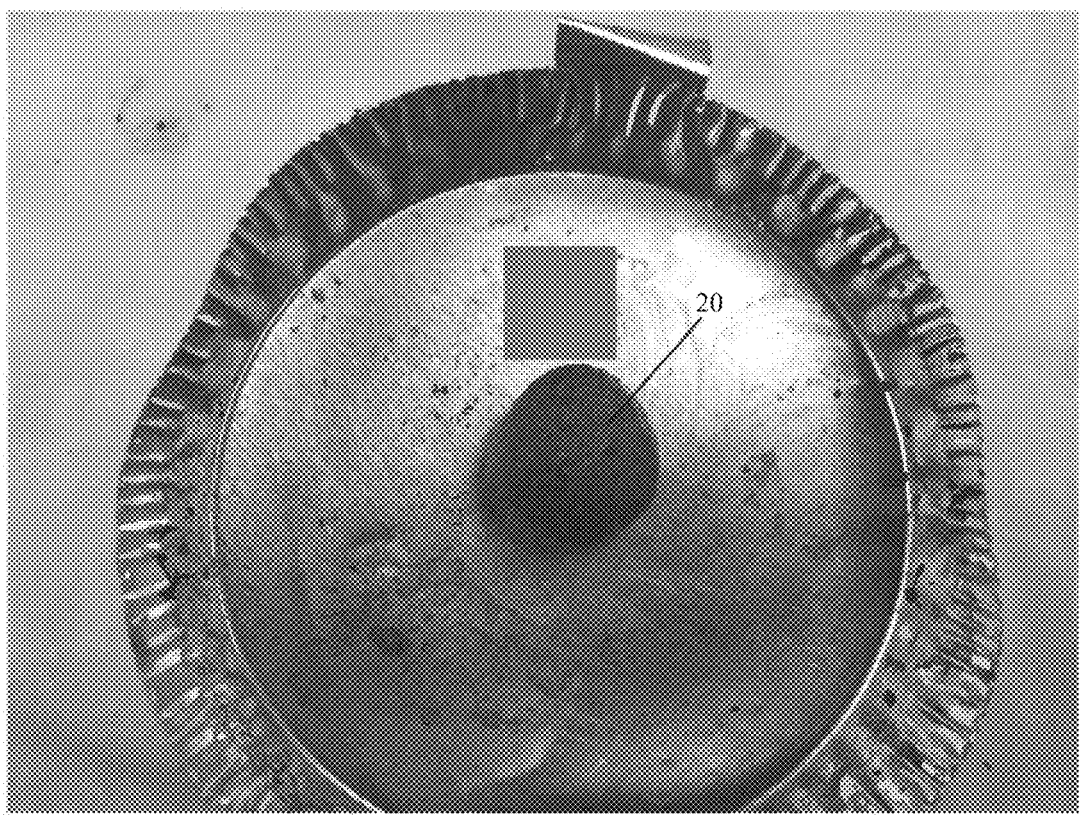
FIG. 3 illustrates a malleable implant after it has been wetted by a fluid. The malleable implant includes a biodegradable polymer such as collagen, mineral particles such as ceramic, and an active agent such as an oxysterol. The malleable implant is moldable into a shape to fit a bone defect.
Figure 4:
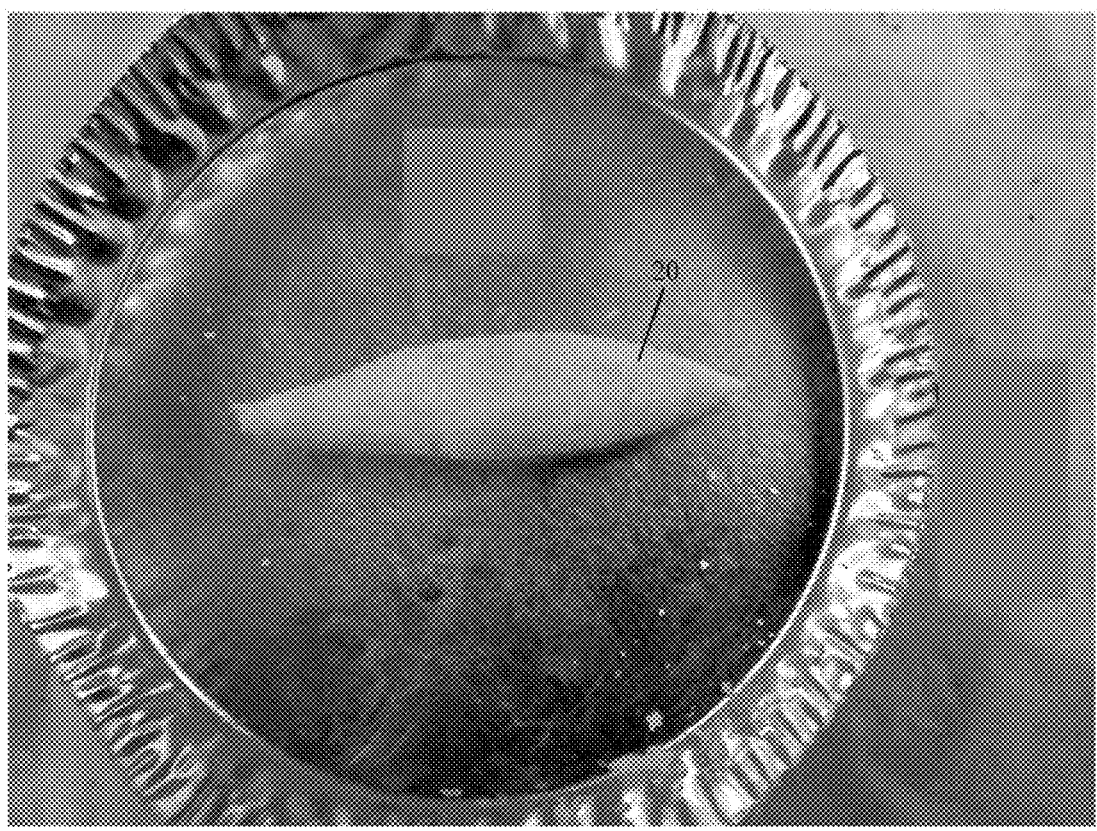
FIG. 4 illustrates a malleable implant after it has been wetted by a fluid. The malleable implant includes a biodegradable polymer such as collagen, mineral particles such as ceramic, and an active agent such as an oxysterol. The malleable implant is moldable into a shape to fit a bone defect.
Figure 5:
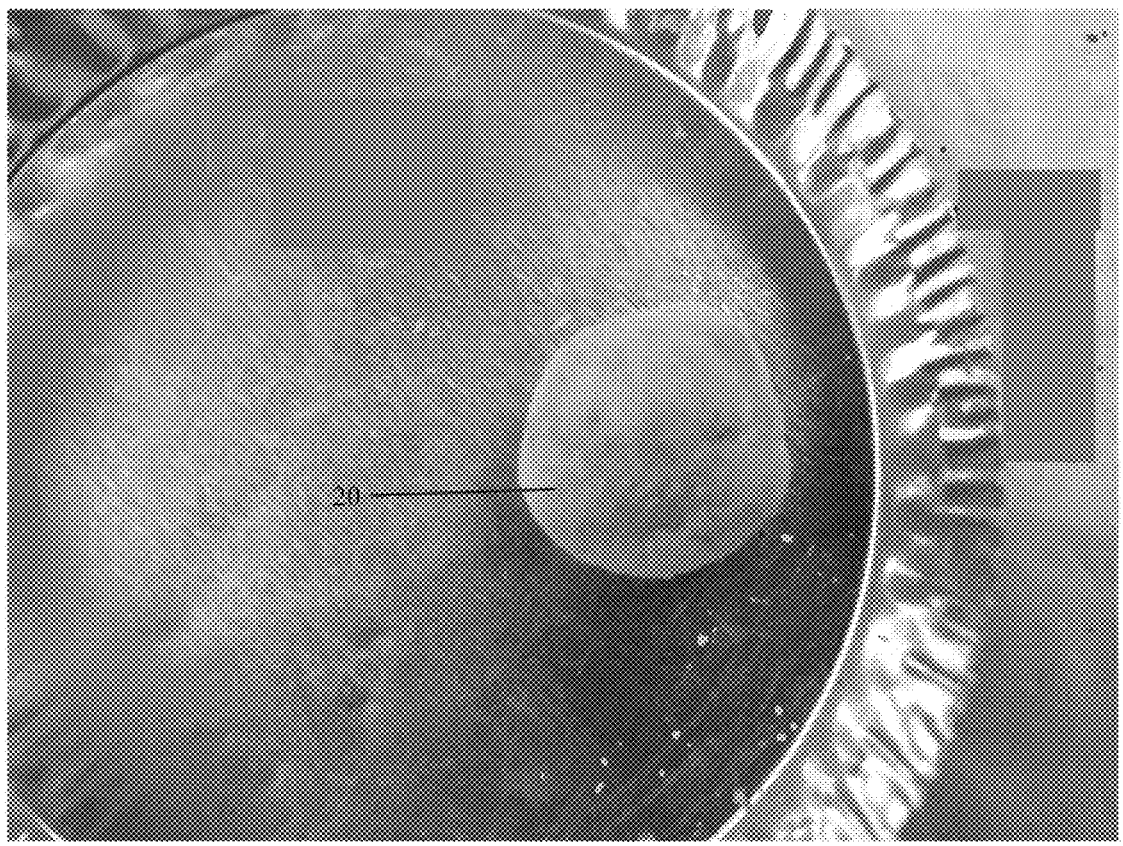
FIG. 5 illustrates a malleable implant after it has been wetted by a fluid. The malleable implant includes a biodegradable polymer such as collagen, mineral particles such as ceramic, and an active agent such as an oxysterol. The malleable implant is moldable into a shape to fit a bone defect.

FIG. 2 illustrates an implant 20 comprising a matrix as shown in FIG. 1 that has been wetted with a suitable fluid. Implant 20 has been wetted with blood to take on a red color, and molded to the shape of a cylinder. FIG. 3 shows implant 20 which has been wetted with blood and molded into a spherical shape. FIG. 4 shows implant 20 which has been wetted with saline to take on a white color, and molded into a cylindrical shape. FIG. 5 shows implant 20 which has been wetted with saline and molded into a spherical shape.

Implant 20 is wetted with a sufficient amount of blood so as to prevent fissuring of the implant when shaped by a medical practitioner. Implant 20 has a biodegradable polymer, mineral particles and oxysterol which are homogenously dispersed such that the implant will have uniform properties throughout. In some embodiments, implant 20 includes regions having disproportionate amounts of one or more components. For example, in some embodiments, implant 20 may have a region of relatively higher concentrated mineral particles to impart increased properties of compression resistance to one or more regions of implant 20.

In some embodiments, the implant comprises a porous matrix configured to allow influx of at least bone and/or cartilage cells therein. In some embodiments, the matrix is also configured to release an active agent, such as an oxysterol. By "porous," it is meant that the matrix has a plurality of pores. The pores of the matrix are a size large enough to allow influx of blood, other bodily fluid, and progenitor and/or bone and/or cartilage cells into the interior to guide the process of tissue formation in vivo in three dimensions.

In some embodiments, the matrix comprises a plurality of pores. In some embodiments, at least 10% of the pores are between about 50 micrometers and about 500 micrometers at their widest points. In some embodiments, at least 20% of the pores are between about 50 micrometers and about 250 micrometers at their widest points. In some embodiments, at least 30% of the pores are between about 50 micrometers and about 150 micrometers at their widest points. In some embodiments, at least 50% of the pores are between about 10 micrometers and about 500 micrometers at their widest points. In some embodiments, at least 90% of the pores are between about 50 micrometers and about 250 micrometers at their widest points. In some embodiments, at least 95% of the pores are between about 50 micrometers and about 150 micrometers at their widest points. In some embodiments, 100% of the pores are between about 10 micrometers and about 500 micrometers at their widest points.

In some embodiments, the matrix has a porosity of at least about 30%, at least about 50%, at least about 60%, at least about 70%, at least about 90% or at least about 95%, or at least about 99%. The pores may support ingrowth of cells, formation or remodeling of bone, cartilage and/or vascular tissue.

In some embodiments, an oxysterol, such as Oxy133, is administered in an implant that is solid or in semi-solid form. The solid or semi-solid form of the device may have a pre-dosed viscosity in the range of about 1 to about 2000 centipoise (cps), 1 to about 200 cps, or 1 to about 100 cps. In various embodiments, the semi-solid or solid implant may comprise a biodegradable polymer having a molecular weight (MW), as shown by the inherent viscosity, from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the matrix has a modulus of elasticity in the range of about $1\times10^2$ to about $6\times10^5$ dyn/cm$^2$, or $2\times10^4$ to about $5\times10^5$ dyn/cm$^2$, or $5\times10^4$ to about $5\times10^5$ dyn/cm$^2$. In some embodiments, the matrix is in the form of a solid or semi-solid.

In some embodiments, the matrix has a density of between about 1.6 g/cra$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than 0.4 g/cm$^3$, less than about 0.3 g/cm$^3$, less than about 0.2 g/cm$^3$, or less than about 0.1 g/cm$^{-3}$.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to till a large the bone defect e.g., osteochondral defect). In some embodiments, at the time of surgery, the matrix can be soaked with an oxysterol and molded by the surgeon to the desired shape to fit the tissue or bone defect.

In some embodiments, the porous interior can hold the oxysterol within the matrix and because the interior is porous, the oxysterol is evenly distributed throughout the matrix when oxysterol is incorporated into the matrix, as discussed herein.

In some embodiments, oxysterol will be held within the interior of the matrix and released into the environment surrounding the matrix (e.g., bone defect, osteochondral defect, etc.) as the matrix degrades over time.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable and cohesive consistency that may subsequently be packed into the bone defect. In some embodiments, the matrix provides a malleable, non-water soluble carrier that permits accurate placement and retention at the implantation site. In some embodiments, the harvested bone and/or cartilage cells can be mixed with the oxysterol and seeded in the interior of the matrix.

Method of Treating

In some embodiments, the implant comprises a biodegradable polymer, mineral particles and an oxysterol, such as, for example, Oxy133, to promote osteogenesis. In use, Oxy133 provides therapeutic treatment for bone conditions. Oxy133 facilitates bone formation, osteoblastic differentiation, osteomorphogenesis and/or osteoproliferation. Treatment can be administered to treat open fractures and fractures at high risk of non-union, and in subjects with spinal disorders. That is, Oxy133 can induce spinal fusion and may help treat degenerative disc disease or arthritis affecting the lumbar or cervical vertebrae.

In some embodiments, the implant is administered by first wetting the matrix to impart malleability and moldability properties to the implant. The implant can be molded to different sizes, shapes and configurations. There are several factors that can be taken into consideration in determining the size, shape and configuration of the implant. For example, both the size and shape may allow for ease in positioning the implant at the target tissue site that is selected as the implantation. In addition, the shape and size of the system should be selected so as to minimize or prevent the implant from moving after implantation. In various embodiments, the implant can be shaped like a rod or a flat surface such as a film or sheet (e.g., ribbon-like) or the like. Flexibility may be a consideration so as to facilitate placement of the device.

Mesenchymal stem cells treated with Oxy133 have increased osteoblast differentiation. Thus, in some embodiments, a matrix comprising Oxy133 may be implanted into a spinal site with mesenchymal stem cells to induce bone growth through osteoblast differentiation. Periosteum tissue is one tissue type that is involved early during normal bone fracture repair process and can recruit various cell types (e.g., mesenchymal stem cells) and bone growth factors necessary for bone fracture repair. Thus, in some embodiments, periosteum tissue is utilized as a source of mesenchymal stem cells and/or growth factors in a demineralized bone composition.

In some embodiments, an implant comprising Oxy133 may be implanted or injected directly to a surgical site on a patient. In some embodiments, the implant is configured to release Oxy133 in the form of a depot. In various embodiments, a plurality of depots (e.g., pellets) can be administered to a surgical site. In some embodiments, a plurality of matrices are provided (e.g., in a kit) and administered to a surgical site and triangulate and/or surround the site needed for bone growth. In various embodiments, a plurality of matrices comprise about 1, 2, 3, 4, 5, 6, 7, 8, 9 or 10 depots. In some embodiments, a plasticizer is used to lower glass translation temperature in order to affect stability of the implant.

Radiographic markers can be included on the implant to permit the user to position it accurately into the target site of the patient. These radiographic markers will also permit the user to track movement and degradation of the implant at the site over time. In this embodiment, the user may accurately position the implant in the site using any of the numerous diagnostic imaging procedures. Such diagnostic imaging procedures include, for example, X-ray imaging or fluoroscopy. Examples of such radiographic markers include, but are not limited to, ceramics, barium, phosphate, bismuth, iodine, tantalum, tungsten, and/or metal beads or particles. In various embodiments, the radiographic marker could be a spherical shape or a ring around the implant. The ceramic in the composition can also be used as a radiographic marker.

In some embodiments, the implant comprising the oxysterol can be administered to the target site by being shaped according to the needs of a medical procedure and passed through a "cannula" or "needle" that can be a part of a delivery device e.g., a syringe, a gun delivery device, or any medical device suitable for the delivery of the implant to a targeted organ or anatomic region. The cannula or needle of the device is designed to cause minimal physical and psychological trauma to the patient.

Biodegradable Polymer

In some embodiments, the matrix comprises a biodegradable polymer, such as, for example, collagen. In some embodiments, the biodegradable polymer is crosslinked. Exemplary collagens include human or non-human (bovine, ovine, piscine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof. In various embodiments, the collagen may be crosslinked.

In some embodiments, the matrix comprises collagen-containing biomaterials from the implant market which, when placed in a bone defect, provide scaffolding around which the patient's new bone and/or cartilage will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos®, marketed by Johnson & Johnson, USA; collagen sponges, e.g. Hemostagene® marketed by Coletica S A, France, or e.g., Helisat® marketed by Integra Life Sciences Inc., USA; and Collagraft® Bone Graft Matrix produced by Zimmer Holdings, Inc., Warsaw, Ind.

In some embodiments, the collagen contains both soluble collagen and insoluble collagen fibers. The soluble collagen and insoluble collagen fibers can first be prepared separately, and then combined. Both the soluble collagen and the insoluble collagen fibers can be derived from a variety of sources, including human, bovine, ovine, piscine, or porcine sources.

In certain embodiments, the matrix includes moldable compositions that include the insoluble collagen fibers at a level of 0.04 g/cc to 0.1 g/cc of the matrix, and soluble collagen at a level of 0.01 g/cc to 0.08 g/cc of the matrix. In other embodiments, such compositions include insoluble collagen fibers at a level of about 0.05 to 0.08 g/cc in the matrix, and soluble collagen at a level of about 0.02 to about 0.05 g/cc in the matrix. In general, the matrix will include insoluble collagen fibers in an amount (percent by weight) that is at least equal to or greater than the amount of soluble collagen, to contribute beneficially to the desired handling and implant properties of the matrix material. In some embodiments, the collagenous matrix will include insoluble collagen fibers and soluble collagen present in a weight ratio of 4:1 to 1:1, more advantageously about 75:25 to about 60:40. In other embodiments, the matrix may include the insoluble collagen fibers and soluble collagen in a weight ratio of about 75:25 to about 65:35, and in one specific embodiment about 70:30.

In some embodiments, the matrix comprises biodegradable polymeric or non-polymeric material. In some embodiments, the matrix may include a biodegradable biopolymer that may provide immediate release, or sustained release of the oxysterol. For example, the biodegradable polymer comprises polyether ether ketone (PEEK). In some embodiments, the matrix may comprise one or more poly (alpha-hydroxy acids), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, chitosan, or combinations thereof.

In some embodiments, the implant may not be fully biodegradable. For example, the device may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylactylamide), PEO-PPO-PEO (pluronics) or combinations thereof. Typically, these types of matrices may need to be removed after a certain amount of time.

In some embodiments, the implant comprises biodegradable polymers comprising wherein the at least one biodegradable polymer comprises one or more of poly(lactide-co-glycolide) (PLGA), polylactide (PLA), polyglycolide (PGA), D-lactide, D,L-actide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof. In some embodiments, the oxysterol is encapsulated in a biodegradable polymer.

In some embodiments, the matrix comprises one or more polymers (e.g., PLA, PLGA, etc.) having a MW of from about 15,000 to about 150,000 Da or from about 25,000 to about 100,000 Da.

In some embodiments, the implant comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the matrix or the implant. In some embodiments, the biodegradable polymer comprises a range of about 0.1% to about 20% based on the total weight of the matrix or the implant. In some embodiments, the biodegradable polymer comprises a range of about 0.1% to about 15% based on the total weight of the matrix or the implant. In some embodiments, the biodegradable polymer comprises 14%, 13%, 12%, 11%, 9%, 8%, 7%, 6%, or 5% based on the total weight of the matrix or the implant.

In some embodiments, the biodegradable polymer is present in an amount of about 0.01 wt % to about 50 wt % or about 8.0 wt % to about 50 wt % of the matrix. In some embodiments, the biodegradable polymer is present in an amount of about 0.1 wt % to about 10 wt %, about 10 wt % to about 20 wt %, about 20 wt % to about 30 wt %, about 30 wt % to about 40 wt %, or about 40 wt % to about 50 wt %.

Mannitol, trehalose, dextran, mPECi and/or PEG may be used as a plasticizer for the polymer. In some embodiments, the polymer and/or plasticizer may also be coated on the implant to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the oxysterol from the implant. In some embodiments, the range of the coating on the implant ranges from about 5 microns to about 250 microns or 5 microns to about 200 microns to delay release from the implant.

Compression resistance is needed for many tissue engineering applications such as tibial plateau fractures, acetabular defects, long bone comminuted fractures, oral maxillofacial defects, spinal fusions, and cartilage subchondral defects. Compression resistant matrices will help facilitate adequate volumes of newly formed bone.

In some embodiments, the matrix is compression resistant where the matrix resists reduction in size or an increase in density when a force is applied as compared to matrices without the elongated particles disposed in it. In various embodiments, the matrix resists compression by at 10%, 15%, 20%, 25%, 30%, 35%, 40%, 45%, 50%, 55%, 60%, 65%, 70%, 75%, 80%, 85%, 90%, 95%, or more in one or all directions when a force is applied to the matrix.

Mineral Particles

In some embodiments, the matrix comprises mineral particles, such as, for example, ceramics. In some embodiments, the particles in the matrix comprise a resorbable ceramic, bone, synthetic degradable polymer, hyaluronic acid, chitosan or combinations thereof. In some embodiments, the particles comprise cortical, cancellous, and/or corticocancellous, allogenic, xenogenic or transgenic bone tissue. The bone component can be fully mineralized or partially or fully demineralized or combinations thereof. The bone component can consist of fully mineralized or partially or fully demineralized bone.

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the matrix may contain an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the matrix, this will act as a local source of calcium and phosphate to the cells attempting to deposit new bone. The inorganic ceramic also provides compression resistance and load bearing characteristics to the matrix.

In some embodiments, the mineral particles in the matrix comprise tricalcium phosphate and hydroxyapatite in a ratio of about 80:20 to about 90:10. In some embodiments, the mineral particles in the matrix comprise tricalcium phosphate and hydroxyapatite in a ratio of about 70:30 to about 95:5. In some embodiments, the mineral particles in the matrix comprise tricalcium phosphate and hydroxyapatite in a ratio of about 85:15.

In some embodiments, the implant can contain demineralized bone material disposed therein. The demineralized bone material can be comprise demineralized bone, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the covering may comprise some fully mineralized bone material. The configuration of the bone material can be obtained by milling, shaving, cutting or machining whole bone as described in for example U.S. Pat. No. 5,899,939. The entire disclosure is herein incorporated by reference into the present disclosure.

In some embodiments, the implant comprises elongated demineralized bone fibers having an average length to average thickness ratio or aspect ratio of the fibers from about 50:1 to about 1000:1. In overall appearance the elongated demineralized bone fibers can be in the form of threads, narrow strips, or thin sheets. The elongated demineralized bone fibers can be substantially linear in appearance or they can be coiled to resemble springs. In some embodiments, the elongated demineralized bone fibers are of irregular shapes including, for example, linear, serpentine or curved shapes. The elongated bone fibers can be demineralized however some of the original mineral content may be retained when desirable for a particular embodiment.

In some embodiments, the implant comprises elongated demineralized bone fibers and chips. In some embodiments, the implant comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the biocompatible material comprises demineralized bone matrix fibers and demineralized bone matrix chips in a 30:60 ratio. In some embodiments, the biocompatible material comprises demineralized bone matrix fibers and demineralized bone matrix chips in a ratio of 25:75 to about 75:25 fibers to chips.

In some embodiments, the matrix comprises mineral particles that offer compression resistance. In some embodiments, the particles comprise at least 10%, 15%, 20%, 25%, 30%, 35%, 40%, 45%, 50%, 55%, 60%, 65%, 70%, 75%, 80%, 85%, 90%, or 95% by weight of the matrix. In some embodiments, the particles are predominantly any shape (e.g., round, spherical, elongated, powders, chips, fibers, cylinders, etc.). In some embodiments, the matrix comprises mineral particles in an amount of about 0.1 wt % to about 95 wt % of the matrix. In some embodiments, the matrix comprises mineral particles in an amount of about 50 wt % to about 80 wt % of the matrix. In some embodiments, the matrix comprises 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, or 79% by weight of the matrix.

In some embodiments, the mineral particles are present in an amount of about 0.1 wt % to about 30 wt % of the matrix. In some embodiments, the mineral particles are present in an amount between about 0.01 wt % to about 50 wt % of the matrix. In some embodiments, the mineral particles are present in an amount between about 7.0 wt % to about 50 wt % of the matrix, in some embodiments, the mineral particles are present in an amount of about 0.1 wt % to about 10 wt %, about 10 wt % to about 20 wt %, about 20 wt % to about 30 wt %, about 30 wt % to about 40 wt %, or about 40 wt % to about 50 wt %.

In some embodiments, the porosity of the particles comprises from 0 to 50%, in some embodiments, the porosity of the particles comprises 5% to 25%. In some embodiments, the particles are not entangled with each other but contact each other and portions of each particle overlap in the matrix to provide compression resistance. In some embodiments, at least 50%, 55%, 60%, 65%, 70%, 75%, 80%, 85%, 90%, 95% or more of the particles overlap each other in the matrix.

In some embodiments, the particles are randomly distributed throughout the matrix. In other embodiments, the particles are uniformly or evenly distributed throughout the matrix. In some embodiments, the particles may be dispersed in the matrix using a dispersing agent. In other embodiments, the particles may be stirred in the polymer and the mechanical agitation will distribute the particles in the matrix until the desired distribution is reached (e.g., random or uniform).

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable and cohesive consistency that may subsequently be packed into the bone defect. In some embodiments, the matrix provides a malleable, non-water soluble carrier that permits accurate placement and retention at the implantation site. In some embodiments, the harvested bone and/or cartilage cells can be mixed with the statin and seeded in the interior of the matrix.

In some embodiments, tissue will infiltrate the matrix to a degree of about at least 50 percent within about 1 month to about 6 months after implantation of the matrix. In some embodiments, about 75 percent of the matrix will be infiltrated by tissue within about 2-3 months after implantation of the matrix. In some embodiments, the matrix will be substantially, e.g., about 90 percent or more, submerged in or enveloped by tissue within about 6 months after implantation of the matrix. In some embodiments, the matrix will be completely submerged in or enveloped by tissue within about 9-12 months after implantation.

Expandable Phase

In some embodiments, the implant may comprise a material, such as, for example, an expandable phase, to facilitate swelling of the implant. The expandable phase comprises polymers that swell upon taking in fluid (e.g., saline, water, bodily fluid, etc.), and thus increase the volume of the implant and which further holds the implant in position over time.

In some embodiments, the expandable phase comprises a range of about 0.1% to about 20% based on the total weight of the matrix or the implant. In some embodiments, the biodegradable polymer comprises a range of about 0.1% to about 10% based on the total weight of the matrix or the implant. In some embodiments, the expandable phase comprises 0.1%, 0.25%, 0.5%, 0.75%, 1%, 2%, 3%, 4%, 5%, 6%, 7%, 8%, 9% or 10% based on the total weight of the matrix or the implant.

In some embodiments, the expandable phase comprises polymers, monomers, starches, gums, poly(amino acids) or a combination thereof that swell upon contact with fluid (water, saline, body fluids, etc.). In various embodiments, the amount of swelling can range from 5 to 100 percent, 5 to 40 percent, or 5 to 20 percent. The time to reach maximum swelling can be varied depending on the location and desired property of the implant. In practice, the time to reach maximum swelling can occur within a period of 5 days, 3 days, 2 days or within a period of 24 hours.

Suitable swellable material may include, for example, hydroxypropyl cellulose, hydroxypropyl methylcellulose, hydroxyethyl methylcellulose, carboxymethylcellulose, hydroxyethylcellulose and salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. In some embodiments, the expandable phase includes gelling polymers including but not limited to cellulosic polymers, vinyl polymers, such as polyvinylpyrrolidone; acrylic polymers and copolymers, such as acrylic acid polymer, methacrylic acid copolymers, ethyl acrytate-methyl methacrylate copolymers, or the like; or mixtures thereof.

A non-limiting list of swellable materials which the expandable phase may comprise include polyvinyl alcohol (PVA), PVA modified with hydrophilic co-monomers, e.g., AMPS, PVA modified with fast crosslinking groups, e.g., NAAADA, PVA modified with polyvinylpyrroline (PVP), carboxymethylcellulose, polyethylene glycol (PEG), poly (vinyl ether), co-polymers of PVA and PEG, polypropylene glycol (PPG), co-polymers of PEG and PPG, co-polymers of PVA or PPG, polyacrylonitrile, hydrocolloids, e.g. agar, alginates, collagen, elastin, chitin, chitosan, gelatin, sugar, mannitol, or the like. In various embodiments, the swellable material includes, for example, poly(N-isopropylacrylamide-co-acrylic acid)-poly(L-lactic acid) (NAL); poly(N-isopropyl acrylamide) (PNIPAM) grafted to other polymers such as carboxymethylcellulose (CMC) copolymers or polymers including block copolymers and end-functionalized polymers, composites or copolymers containing thermosensitive poly(2-ethoxyethyl vinyl ether) and/or poly(hydroxyethyl ether) and/or (EOVE200-HOVE400), whose sol-gel transition temperature is 20.5° C. The swellable material, in various embodiments, may be used to control release of the oxysterol into the tissue and/or the synovial space.

In some embodiments, the expandable phase includes hyaluronic acid. In some embodiments, the expandable phase includes glycosaminoglycans. Non-limiting examples of glycosaminoglycans include chondroitin sulfate, dermatan sulfate, keratin sulfate, heparin, heparan sulfate, and hyaluronan. In some embodiments, the expandable phase includes mannitol, PEG, magnesium alginate or glycerol.

The polymers may be crosslinked, lightly crosslinked hydrophilic polymers. Although these polymers may be non-ionic, cationic, zwitterionic, or anionic, in various embodiments, the swellable polymers are cationic or anionic. In various embodiments, the swellable polymer may contain a multiplicity of acid functional groups, such as carboxylic acid groups, or salts thereof. Examples of such polymers suitable for use herein include those which are prepared from polymerizable, acid-containing monomers, or monomers containing functional groups which can be converted to acid groups after polymerization. Examples of such polymers also include polysaccharide-based polymers such as carboxymethyl starch and cellulose, and poly(amino acid) polymers such as poly(aspartic acid). Some non-acid monomers may also be included, usually in minor amounts, in preparing the absorbent polymers. Such non-acid monomers include, for example, monomers containing the following types of functional groups: carboxylate or sulfonate esters, hydroxyl groups, amide groups, amino groups, nitrile groups, quaternary ammonium salt groups, and aryl groups (e.g. phenyl groups, such as those derived from styrene monomer). Other potential non-acid monomers include unsaturated hydrocarbons such as ethylene, propylene, 1-butene, butadiene, or isoprene.

In some embodiments, the expandable phase comprises substances which are capable of becoming freely permeable following hydration in aqueous fluids. Such substances include polysaccharides, such as gelatin, saccharide, sorbitol, mannanes, jaluronic acid, polyaminoacids, polyalcohols, polyglycols, or the like. In addition to the foregoing, the swellable polymer may also include additional excipients such as lubricants, flow promoting agents, plasticizers, and anti-sticking agents. For example, the expandable phase may further include polyethylene glycol, polyvinylpyrrolidone, talc, magnesium stearate, glyceryl behenate, stearic acid, or titanium dioxide.

In various embodiments, the particle size distribution of the expandable phase material may be about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

Method of Making Matrix

In some embodiments, the matrix is made by adding an oxysterol in an amount of about 20 wt % to about 90 wt % to a biodegradable polymer, the biodegradable polymer being in an amount of about 0.1 wt % to about 20 wt % based on the total weight of the implant to form a mixture. In some embodiments, the mixture forms a slurry. The porous ceramic particles are added to the mixture to form the implant, the porous ceramic particles being in an amount of about 30 wt % to about 99.5 wt % based on a total weight of the implant. In some embodiments, the matrix is dried, hardened or cured to form the implant.

In some embodiments, in manufacturing the implant, a mixture of the matrix material (e.g., collagen and oxysterol) is combined with the mineral particles and a liquid to wet the material and form a putty or paste. Any suitable liquid can be used including, for example, aqueous preparations such as water, saline solution (e.g. physiological saline), sugar solutions, erotic organic solvents, or liquid polyhydroxy compounds such as glycerol and glycerol esters, or mixtures thereof. The liquid may, for example, constitute about 5 to about 70 weight percent of the mixed composition prior to the molding operation. Once wetted, the implant becomes moldable and may be shaped by a medical practitioner by hand.

In one embodiment of manufacture, a collagen mixture can be combined with mineral particles, an oxysterol and a liquid, desirably with an aqueous preparation, to form a moldable cohesive mass. Excess liquid can be removed by any suitable means, including for example by applying the cohesive mass to a liquid-permeable mold or form and draining away excess liquid.

In some embodiments, the implant is formed by mixing the mineral particles, polymer and the oxysterol until a coherent mass is formed. In some embodiments, the mineral particles, polymer and the oxysterol are wetted and mixed in a mixing syringe or device.

In some embodiments, the mixture of the polymer, mineral particles and/or oxysterol are molded to take the form of the implant. Before, during or after molding, including in some instances the application of compressive force to the matrix, the biodegradable polymer can be subjected to one or more additional operations such as heating, lyophilizing and/or crosslinking. In this regard, crosslinking can be used to improve the strength of the formed matrix. Alternatively, the surface of the matrix can be crosslinked to reduce the size of the pores of the porous interior and thereby form the exterior of the matrix that is less permeable and/or less porous than a porous interior. Crosslinking can be achieved, for example, by chemical reaction, the application of energy such as radiant energy (e.g., UV light or microwave energy), drying and/or heating and dye-mediated photo-oxidation; dehydrothermal treatment; enzymatic treatment or others.

In some embodiments, a chemical crosslinking agent is used. Examples of suitable cross-linking agents include those that contain bifunctional or multifunctional reactive groups, and which react with the matrix. Chemical crosslinking can be introduced by exposing the matrix material to a chemical crosslinking agent, either by contacting it with a solution of the chemical crosslinking agent or by exposure to the vapors of the chemical crosslinking agent. This contacting or exposure can occur before, during or after a molding operation. In any event, the resulting material can then be washed to remove substantially all remaining amounts of the chemical crosslinker if needed or desired for the performance or acceptability of the final implantable matrix.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; and/or sugars, including glucose, will also crosslink the matrix material.

In some embodiments, the matrices are formed by mixing the oxysterol with a polymer slurry such as collagen and pouring into a shaped mold. The composite mixture is freeze dried and possibly chemically crosslinked and cut to the final desired shape.

In some embodiments, the oxysterol is solubilized and mixed with the biodegradable polymer. In some embodiments, the oxysterol is solubilized in an organic solvent (i.e., ethanol) or optionally with a co-solvent (i.e., PEG). Suitable examples of organic solvents include tetrahydrofuran, diethyl ether, dichloromethane, ethyl acetate, acetone, n,n-dimethylformamide, acetonitrile, dimethyl sulfoxide, ammonia, t-butanol, n-propanol, ethanol, methanol, acetic acid or combinations thereof. In some embodiments, the oxysterol may be mixed in a 25:75 to a 75:25 ratio with the solvent. In some embodiments, the oxysterol is mixed in a 50:50 ratio with the solvent to form a solution or suspension of the oxysterol, which can then be added to the polymer matrix or the ceramic particles.

For example, if the oxysterol is Oxy133, it is typically only slightly soluble or insoluble in water. The Oxy133 can be solubilized in a non-aqueous solvent, such as for example, ethanol and mixed into a solution or suspension. In some embodiments, the Oxy133 can be filtered by passing the Oxy133 and solvent through a filter (e.g., 0.22 microns). This will remove bacteria and other larger-size particulates out of the composition. The Oxy133 used in the composition can be micronized before it is mixed with solvents and other excipients. In various embodiments, the particle size of the Oxy133 can range from about 1 micron to 250 microns. In some embodiments, the Oxy133 can have a particle size of from about 5 microns to about 100 microns or from about 20 to 50 microns. The Oxy133 in the solution or suspension can be added to a slurry of biodegradable polymer and/or the ceramic particles, mixed and, then optionally dried.

The implant may be used to repair bone and/or cartilage at a target tissue site, e.g., one resulting from injury, defect brought about during the course of surgery, infection, malignancy or developmental malformation. The implant can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones which can be repaired or replaced with the implantable matrix herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

Application of the Oxysterol to the Matrix

In some embodiments, a therapeutic agent (oxysterol, with or without one or more growth factors, etc.) may be disposed on or in the implant by hand, spraying, impregnating, injecting, brushing and/or pouring it to infuse the implant.

Application of the oxysterol to the implant may occur at the time of surgery or by the manufacturer or in any other suitable manner. For example, the oxysterol may be further reconstituted using a syringe and the syringe can be placed into the interior of the implant via insertion of a needle or cannula (piercing the matrix) and placing it into the interior of the implant and injecting the oxysterol so it is evenly distributed throughout the porous interior.

In some embodiments, the oxysterol may be applied to the matrix prior to combining the materials and forming it into the final implant shape. Indeed, the oxysterol can be blended into the natural or synthetic polymer (i.e., collagen) and poured into molds of the final shape of the implant. Alternatively, the oxysterol, such as Oxy133, may be applied onto and/or into the porous loaded matrix after forming it into the final shape by soaking, dripping, injecting, spraying, etc.

In some embodiments, the interior of the implant is loaded with oxysterol that functions as an osteoinductive factor. In some embodiments, the oxysterol can be disposed in a vial and then a surgeon can mix a fluid with the oxysterol, which can be used to load the implant with the oxysterol.

The amount of oxysterol, may be sufficient to cause bone and/or cartilage growth. In some embodiments, the oxysterol is Oxy133 and is contained in one or more matrices in an amount of from 1 to 2 mg per cubic centimeter of the matrix.

In some embodiments, the oxysterol is supplied in a liquid carrier (e.g., an aqueous buffered solution or organic solvent). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the oxysterol is provided in a vehicle (including a buffer) containing sucrose, glycine, L-glutamic acid, sodium chloride, and/or polysorbate 80. Exemplary organic solvents or non-aqueous solvents include DMSO, acetic acid, acetone, DME, DMF, MTBE, acetonitrile, butanol, butanone, t-butyl alcohol, ethanol, polyethylene glycol, methanol, chlorobenzene, chloroform, toluene, propanol, pentane, heptane, ethanol, diethyl ether, or the like.

Additional Therapeutic Agents

In some embodiments, the implant further comprises oxysterol and one or more additional therapeutic agents including one or more growth factors, statins, etc. Isolated osteoinductive agents that are included within a matrix are typically sterile. In a non-limiting method, sterility is readily accomplished for example by filtration through sterile filtration membranes (e.g., 0.2 micron membranes or filters). In one embodiment, the matrix includes osteoinductive agents comprising one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the preferred osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can be used at a concentration of about 0.4 mg/ml to about 10.0 mg/ml, (preferably near 1.5 mg/ml. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In addition to the above, the matrix may include one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The growth factors and the oxysterol of the present application may be disposed on or in the matrix with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine, statins or the like.

Examples of therapeutic agents suitable for use also include, but are not limited to, an anti-inflammatory agent, analgesic agent, or osteoinductive growth factor or a combination thereof.

Kits

The biodegradable polymer, mineral particles, oxysterol and devices to administer the implant may be sterilizable. In various embodiments, one or more components of the matrix, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the implantable matrix may be packaged in a moisture resistant package and then terminally sterilized by gamma irradiation. In use the surgeon removes the one or all components from the sterile package for use.

In various embodiments, electron beam (re-beam) radiation may be used to sterilize one or more components of the matrix. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implantable matrix and/or one or more components of the matrix, including, but not limited to, gas sterilization, such as, for example, with ethylene oxide or steam sterilization.

In various embodiments, a kit is provided comprising the oxysterol, matrix, mineral particles, and/or diluents. The kit may include additional parts along with the implantable matrix combined together to be used to implant the matrix (e.g., wipes, needles, syringes, mixing syringe or other mixing device, etc.). The kit may include the matrix in a first compartment. The second compartment may include a vial holding the oxysterol, diluent and any other instruments needed for the localized delivery. A third compartment may include gloves, drapes, wound dressings and other procedural supplies for maintaining sterility of the implanting process, as well as an instruction booklet, which may include a chart that shows how to implant the matrix after reconstituting it. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

These and other aspects of the present application will be further appreciated upon consideration of the following Examples, which are intended to illustrate certain particular embodiments of the application but are not intended to limit its scope, as defined by the claims.

EXAMPLES

Example 1

A first formulation of the moldable implant was prepared having a composition as shown in Table 1.

TABLE 1

| % CMC | % Collagen | % Ceramic | % Oxy133 |
| --- | --- | --- | --- |
| 4 | 12 | 80 | 5 |
| 4 | 13 | 54 | 30 |
| 2 | 12 | 80 | 5 |
| 2 | 13 | 54 | 30 |

The values listed in Table 2 refer to the composition of the dry powder components of the matrix prior to being wetted with physiologically acceptable saline. The carboxymethylcellulose was added to impart the implant with adhesive properties. It was found that the carboxymethylcellulose also caused the implant to significantly expand upon wetting. In some cases, the carboxymethylcellulose expanded the implant to twice the size of the dry compound in some dimensions. The collagen added to the composition was porcine fibrillar Type I collagen. The ceramic comprised beta tri-calcium phosphate and hydroxyapatite in a ratio of 85:15. The ceramic particles had a particle size of about 125 µm to about 750 µm. Small particles were preferred to create a larger surface area-to-volume ratio to provide for faster resorption after implantation in a bony defect. A relatively high amount of ceramic was provided to the composition to impart properties of compression resistance. Oxy133 was added to the composition at an amount of about 400 mg/cc. The Oxy133 added was in the crystalline form of a monohydrate.

Example 2

A formulation of the moldable implant was prepared having a composition as shown in Table 2.

TABLE 2

| % Collagen | % Ceramic | % Oxy133 |
| --- | --- | --- |
| 8 | 51 | 41.5 |

The values listed in Table 2 refer to the composition of the powder components of the matrix prior to being wetted with physiologically acceptable saline. Upon being wetted, it was found that the collagen held the implant together with little to no crosslinking. The collagen added to the composition was porcine fibrillar Type 1 collagen. The ceramic comprised beta tri-calcium phosphate and hydroxyapatite in a ratio of 85:15. The ceramic particles had a particle size of about 125 µm to about 750 µm. Small particles were preferred to create a larger surface area to volume ratio to provide faster resorption after implantation in a bony defect. A relatively high amount of ceramic was provided to the composition to impart properties of compression resistance. Oxy133 was added to the composition at a level of about 400 mg/cc. The Oxy133 added was in the crystalline form of a monohydrate.

Example 3

Compositions were prepared according to the specifications of Examples 1 or 2 above. The compositions were wetted with sterilized water.

Example 4

Compositions were prepared according to the specifications of Examples 1 or 2 above. The compositions were wetted with blood.

Example 5

Compositions were prepared according to the specifications of Examples 1 or 2 above. The compositions were wetted with bone marrow aspirate.

Example 6

A dry composition of a matrix containing Oxy133, collagen, and ceramic particles as described herein was prepared and wetted with 1.4 cc of heparinized rabbit blood. The matrix was rolled into a ball and a cylinder. It was observed that the shaped matrix showed slight fissuring, and an additional 0.3 cc of heparinized rabbit blood was added to the matrix. The added wetting fluid allowed the matrix to be shaped with no fissuring.

Example 7

A dry composition of a matrix containing Oxy133, collagen, ceramic particles, and carboxymethylcellulose as described herein was prepared. The dry matrix was incrementally wetted with heparinized rabbit blood. It was found that volumes below about 1.3 cc of blood were ineffective in adequately wetting the matrix. After 1.43 cc of blood had been added, the matrix was rolled into a cohesive ball and cylinder shapes with no fissuring. Carboxymethylcellulose was found to provide cohesiveness and adhesiveness to the matrix.

Example 8

A dry composition of a matrix containing Oxy133, collagen, and ceramic particles as described herein was prepared and wetted with 1.46 cc of physiologically acceptable saline. Fresh bone graft was obtained from the iliac crest of rabbits. The bone chips were progressively added to the matrix. The matrix cohesively rolled into a ball and cylinder shapes with no fissuring when up to an amount of 2.0 cc of bone graft was added.

Example 9

Figure 6:
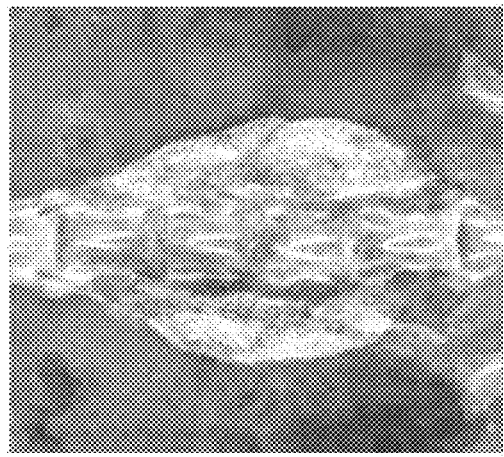
FIG. 6 illustrates uses of a formulation of malleable implants having 20 mg of Oxy133 on each side of the implant, in accordance with the malleable implants described herein.
Figure 6:
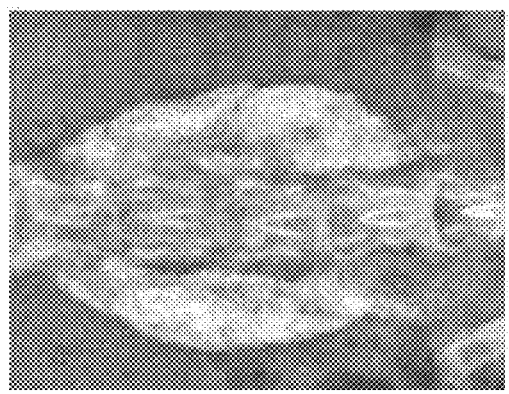
Figure 6:
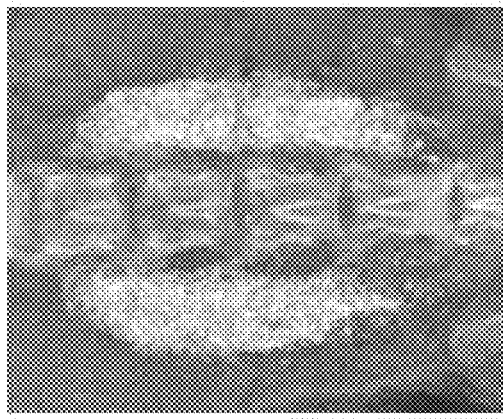

A dry composition of a matrix containing Oxy133, collagen and ceramic as described herein was prepared and wetted with sterile water to be implanted in rat spines as shown in FIG. 6. The wetted matrix was cut in half with a razor blade to yield two halves. The two implants were molded into cylindrical shapes prior to insertion and were positioned bilaterally in the posterolateral space of each test subject. Each implant contained 20 mg Oxy133. Radiographs were taken roughly 10 minutes after the procedure, 4 weeks after the procedure, and 8 weeks after the procedure. As shown in FIG. 6, the implants promoted bridging bone across the transverse processes of L3-L5 at the 4-week and 8-week timepoints. Fusion was tested at 8-week sacrifice by manual palpation. The section of the spine where the implants were located showed limited flexibility in the manual palpation evaluation, indicating that fusion had occurred. In this study, fusion was observed in 5/5 (100%) of the rat spines receiving the described formulation.

Example 10

A dry composition of a matrix containing Oxy133, collagen and ceramic as described herein was prepared and wetted with sterile water to be implanted in rat spines as shown in FIG. 6. The wetted matrix was cut in half with a razor blade to yield two halves. The two implants were molded into cylindrical shapes prior to insertion and were positioned bilaterally in the posterolateral space of each test subject. Each implant contained 125 mg Oxy133. Radiographs were taken roughly 10 minutes after the procedure, 4 weeks after the procedure, and 8 weeks after the procedure. As shown in FIG. 6, the implants promoted bridging bone across the transverse processes of L3-L5 at the 4-week and 8-week timepoints. Fusion was tested at 8-week sacrifice by manual palpation. The section of the spine where the implants were located showed limited flexibility in the manual palpation evaluation, indicating that fusion had occurred. In this study, fusion was observed in 5/5 (100%) of the rat spines receiving the described formulation.

All patent and non-patent publications cited in this disclosure are incorporated herein in to the extent as if each of those patent and non-patent publications was incorporated herein by reference in its entirety. Further, even though the disclosure herein has been described with reference to particular examples and embodiments, it is to be understood that these examples and embodiments are merely illustrative of the principles and applications of the present disclosure. It is therefore to be understood that numerous modifications may be made to the illustrative embodiments and that other arrangements may be devised without departing from the spirit and scope of the present disclosure as defined by the following claims.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implant configured to fit at or near a bone defect to promote bone growth, the implant comprising: a biodegradable polymer comprising porcine-derived collagen, the biodegradable polymer in an amount of about 8 wt % of the implant; a mixture of beta tricalcium phosphate and hydroxyapatite in a ratio of 85:15, the mixture in an amount of about 50 wt % of the implant; and an oxysterol comprising (3S,5S,6S,8R,9S,10R,13S,14S,17S)17-((S)-2-hydroxyoctan-2-yl)-10,13-dimethylhexadecahydro-1H-cyclopenta[a]phenanthrene-3,6-diol (Oxy133) in monohydrate form, the oxysterol in an amount of about 41.5 wt % of the implant, wherein the Oxy133 has a particle size of from about 5 microns to about 100 microns.

2. An implant according to claim 1, wherein the implant is moldable and comprises autograft bone particles, allograft bone particles or xenograft bone particles.

3. An implant according to claim 1, wherein the implant is configured to form a coherent mass and be moldable after being wetted with a fluid.

4. An implant according to claim 1, wherein (i) the biodegradable polymer is crosslinked; or (ii) the biodegradable polymer is uncrosslinked.

5. An implant according to claim 1, wherein the biodegradable polymer further comprises human-derived collagen, bovine-derived collagen, piscine-derived collagen, ovine-derived collagen, recombinant collagen, gelatin, or combinations thereof.

6. An implant according to claim 3, wherein the fluid comprises water, sodium chloride, dextrose, Lactated Ringer's solution, blood, bone marrow or a combination thereof.

7. A method for making an implant, the method comprising adding an oxysterol to a biodegradable polymer containing a mixture of beta tricalcium phosphate and hydroxyapatite to form the implant; wherein the oxysterol comprises (3S,5S,6S,8R,9S,10R,13S,14S,17S)17-((S)-2-hydroxyoctan-2-yl)-10,13-dimethylhexadecahydro-1H-cyclopenta[a]phenanthrene-3,6-diol (Oxy133) in monohydrate form, the oxysterol is in an amount of about 41.5 wt % based on a total weight of the implant, and the Oxy133 has a particle size of from about 5 microns to about 100 microns; the biodegradable polymer comprises porcine-derived collagen, the biodegradable polymer is in an amount of about 8 wt % based on the total weight of the implant; and the mixture of beta tricalcium phosphate and hydroxyapatite is in a ratio of 85:15 and is in an amount of about 50 wt % based on the total weight of the implant.

8. An implant according to claim 1, wherein the oxysterol is uniformly distributed throughout the biodegradable polymer, and/or the oxysterol is uniformly distributed throughout the mineral particles.

* * * * *